United States Patent
Craig

(10) Patent No.: US 7,060,506 B2
(45) Date of Patent: Jun. 13, 2006

(54) COMPOSITIONS AND METHODS FOR MONITORING THE MODIFICATION OF MODIFICATION DEPENDENT BINDING PARTNER POLYPEPTIDES

(75) Inventor: Roger Craig, Smallwood (GB)

(73) Assignee: Cyclacel, Ltd. (GB)

( * ) Notice: Subject to any disclaimer, the term of this patent is extended or adjusted under 35 U.S.C. 154(b) by 157 days.

(21) Appl. No.: 09/770,102

(22) Filed: Jan. 25, 2001

(65) Prior Publication Data
US 2002/0197606 A1 Dec. 26, 2002

Related U.S. Application Data

(60) Provisional application No. 60/179,283, filed on Jan. 31, 2000.

(51) Int. Cl.
*G01N 33/543* (2006.01)
(52) U.S. Cl. .......................... 436/518; 435/6; 435/7.1; 435/7.4; 436/164; 436/524
(58) Field of Classification Search .................... 435/6, 435/7.1, 68.1, 7.4, 961, 524; 436/501, 518, 436/56, 546, 164, 172
See application file for complete search history.

(56) References Cited

U.S. PATENT DOCUMENTS

| | | | |
|---|---|---|---|
| 5,283,173 A | 2/1994 | Fields et al. | 435/6 |
| 5,503,977 A | 4/1996 | Johnsson et al. | 435/6 |
| 5,582,995 A | 12/1996 | Avruch et al. | 435/71 |
| 5,637,463 A | 6/1997 | Dalton et al. | 435/6 |
| 5,863,726 A | 1/1999 | Harley et al. | 435/6 |
| 5,962,289 A | 10/1999 | Kilburn et al. | 435/179 |
| 5,962,637 A | 10/1999 | Shone et al. | 530/329 |
| 5,965,699 A | 10/1999 | Schmidt et al. | 530/326 |
| 5,981,167 A | 11/1999 | Taremi et al. | 435/4 |
| 6,146,842 A | 11/2000 | Josiah et al. | 435/15 |
| 6,242,173 B1 | 6/2001 | Mann et al. | 435/4 |
| 6,243,980 B1 | 6/2001 | Bronstein et al. | 43/7.72 |
| 6,268,123 B1 | 7/2001 | Faff | 435/5 |
| 6,312,896 B1 * | 11/2001 | Heroux et al | 435/6 |
| 6,322,970 B1 | 11/2001 | Little et al. | 435/6 |
| 6,465,199 B1 * | 10/2002 | Colyer et al. | 435/7.4 |
| 2002/0197696 A1 * | 12/2002 | Levin et al | 435/200 |

FOREIGN PATENT DOCUMENTS

| | | | |
|---|---|---|---|
| WO | WO 92/00388 | | 1/1992 |
| WO | WO 97/28261 | | 8/1997 |
| WO | WO 98/06737 | | 2/1998 |
| WO | WO 98/44350 | * | 10/1998 |
| WO | WO 9911774 | * | 3/1999 |

OTHER PUBLICATIONS

Wild et al., The Immunoassay Handbook, Signal Generation and Detection Systems, p. 63-65, 1994.*
Matyus (1992). "Fluorescence resonance energy transfer measurements on cell surfaces. A spectroscopic tool for determining protein interactions," *J. Photochem. Photobiol. B: Biology* 12:323.
Latour, et al. (1996). "Differential Intrinsic Enzymatic Activity of Syk and Zap-70 Protein-tyrosine Kinases," J. Bio. Chem. 271(37):22782-22790.

* cited by examiner

*Primary Examiner*—Long V. Le
*Assistant Examiner*—Gary W. Counts
(74) *ttorney, Agent, or Firm*—Kathleen M. Williams; Mark J. FitzGerald; Palmer & Dodge, LLP

(57) ABSTRACT

The invention provides methods and compositions for monitoring enzymatic activity as a function of the interaction of modification dependant binding partner polypeptides. Association or dissociation of the binding partner polypeptides is dependant upon the addition or removal of a moiety to or from one or both of the binding partner polypeptides or upon proteolytic digestion of one or both of the binding partner polypeptides by a modifying enzyme.

18 Claims, 8 Drawing Sheets

COMPOSITIONS AND METHODS FOR MONITORING THE MODIFICATION OF MODIFICATION DEPENDENT BINDING PARTNER POLYPEPTIDES

This application claims the priority of U.S. Provisional Application No. 60/179,283, filed Jan. 31, 2000.

FIELD OF THE INVENTION

The invention relates to monitoring of enzymatic modification dependant polypeptide interaction.

BACKGROUND OF THE INVENTION

The modification, including the post-translational modification, of proteins have been known for over 40 years and since then has become a ubiquitous feature of protein structure. The addition of biochemical groups to translated polypeptides has wide-ranging effects on protein stability, protein secondary and tertiary structure, enzyme activity, and in more general terms on the regulated homeostasis of cells. Such modifications include, but are not limited to, the addition of a phosphate (phosphorylation), carbohydrate (glycosylation), ADP-ribosyl (ADP ribosylation), fatty acid (prenylation, which includes but is not limited to: myristoylation and palmitylation), ubiquitin (ubiquitination) and sentrin (sentrinization; a ubiquitination-like protein modification) or the proteolytic digestion of a protein (proteolysis). Additional examples of modification include methylation, acetylation, hydroxylation, iodination, and flavin linkage. Many of the identified modifications have important consequences for the activity of those polypeptides so modified.

Phosphorylation is a well-studied example of a post-translational modification of protein. There are many cases in which polypeptides form higher order tertiary structures with like polypeptides (homo-oligomers) or with unlike polypeptides (hetero-oligomers). In the simplest scenario, two identical polypeptides associate to form an active homodimer. An example of this type of association is the natural association of myosin II molecules in the assembly of myosin into filaments.

The dimerization of myosin II monomers is the initial step in seeding myosin filaments. The initial dimerization is regulated by phosphorylation the effect of which is to induce a conformational change in myosin II secondary structure resulting in the folded 10S monomer subunit extending to a 6S molecule. This active molecule is able to dimerize and subsequently to form filaments. The involvement of phosphorylation of myosin II in this priming event is somewhat controversial. Although in higher eukaryotes the conformational change is dependent on phosphorylation, in Ancanthoamoeba, a lower eukaryote, the post-translational addition of phosphate is not required to effect the initial dimerization step. It is of note that the dimerization domains in myosin II of higher eukaryotes contain the sites for phosphorylation and it is probable that phosphorylation in this region is responsible for enabling myosin II to dimerize and subsequently form filaments. In Dictyostelium this situation is reversed in that the phosphorylation sites are outside the dimerization domain and phosphorylation at these sites is required to effect the disassembly of myosin filaments. In contrast to both these examples, Acanthoamoeba myosin II is phosphorylated in the dimerization domain but this modification is not necessary to enable myosin II monomers to dimerize in this species.

By far the most frequent example of post-translational modification is the addition of phosphate to polypeptides by specific enzymes known as protein kinases. These enzymes have been identified as important regulators of the state of phosphorylation of target proteins and have been implicated as major players in regulating cellular physiology. For example, the cell-division cycle of the eukaryotic cell is primarily regulated by the state of phosphorylation of specific proteins the functional state of which is determined by whether or not the protein is phosphorylated. This is determined by the relative activity of protein kinases which add phosphate and protein phosphatases which remove the phosphate moiety from these proteins. Clearly, dysfunction of either the kinases or phosphatases may lead to a diseased state. This is best exemplified by the uncontrolled cellular division shown by tumor cells. The regulatory pathway is composed of a large number of genes that interact in vivo to regulate the phosphorylation cascade that ultimately determines if a cell is to divide or arrest cell division.

Currently there are several approaches to analyzing the state of modification of target proteins in vivo and in vitro:

1. In vivo labeling of cellular substrate pools with radioactive substrate or substrate precursor molecules to result in incorporation of labeled (for example, radiolabeled) moieties (e.g., phosphate, fatty acyl (including, but not limited to, myristoyl, palmityl), sentrin, methyl, acetyl, hydroxyl, iodine, flavin, ubiquitin or ADP-ribosyls), which are added to target proteins. Analysis of modified proteins is typically performed by electrophoresis and autoradiography, with specificity enhanced by immunoprecipitation of proteins of interest prior to electrophoresis.
2. Back-labeling. The enzymatic incorporation of a labeled (including, but not limited to, with a radioactive and fluorescent label) moiety into a protein in vitro to estimate the state of modification in vivo.
3. Detection of alteration in electrophoretic mobility of modified protein compared with unmodified (e.g., glycosylated or ubiquitinated) protein.
4. Thin-layer chromatography of radiolabeled fatty acids extracted from the protein of interest.
5. Partitioning of protein into detergent-rich or detergent layer by phase separation, and the effects of enzyme treatment of the protein of interest on the partitioning between aqueous and detergent-rich environments.
6. The use of cell-membrane-permeable protein-modifying enzyme inhibitors (e.g., Wortmannin, staurosporine) to block modification of target proteins and comparable inhibitors of the enzymes involved in other forms of protein modification (above).
7. Antibody recognition of the modified form of the protein (e.g., using an antibody directed at ubiquitin or carbohydrate epitopes), e.g., by Western blotting, of either 1- or 2-dimensional gels bearing test protein samples.
8. Lectin-protein interaction in Western blot format as an assay of the presence of particular carbohydrate groups (defined by the specificity of the lectin in use).
9. The exploitation of eukaryotic microbial systems to identify mutations in protein-modifying enzymes.

These strategies have certain limitations. Monitoring states of modification by pulse or steady-state labeling is merely a descriptive strategy to show which proteins are modified when samples are separated by gel electrophoresis and visualized by autoradiography. This is unsatisfactory, due to the inability to identify many of the proteins that are modified. A degree of specificity is afforded to this technique if it is combined with immunoprecipitation; however, this is of course limited by the availability of antibodies to target proteins. Moreover, only highly-expressed proteins are readily detectable using this technique, which may fail to identify many low-abundance proteins, which are potentially important regulators of cellular functions.

Finally, yeast (*Saccharomyces cerevisiae* and *Schizosaccharomyces pombe*) has been exploited as a model organism for the identification of gene function using recessive mutations. It is through research on the effects of these mutations that the functional specificities of many protein-modifying enzymes have been elucidated. However, these molecular genetic techniques are not easily transferable to higher eukaryotes, which are diploid and therefore not as genetically tractable as these lower eukaryotes.

An example of heterodimer association is described in patent application number WO92/00388. It describes an adenosine 3:5 cyclic monophosphate (cAMP) dependent protein kinase which is a four-subunit enzyme being composed of two catalytic polypeptides (C) and two regulatory polypeptides (R). In nature the polypeptides associate in a stoichiometry of $R_2C_2$. In the absence of cAMP the R and C subunits associate and the enzyme complex is inactive. In the presence of cAMP the R subunit functions as a ligand for cAMP resulting in dissociation of the complex and the release of active protein kinase. The invention described in WO92/00388 exploits this association by adding fluorochromes to the R and C subunits.

The polypeptides are labeled (or 'tagged') with fluorophores having different excitation/emission wavelengths. The emission from one such fluorophore following excitation effects a second excitation/emission event in the second fluorophore. By monitoring the fluorescence emission or absorption of each fluorophore, which reflects the presence or absence of fluorescence energy transfer between the two, it is possible to derive concentration of cAMP as a function of the association between the R and C subunits. Therefore, the natural affinity of the C subunit for the R subunit has been exploited to monitor the concentration of a specific metabolite, namely cAMP.

The prior art teaches that intact, fluorophore-labeled proteins can function as reporter molecules for monitoring the formation of multi-subunit complexes from protein monomers; however, in each case, the technique relies on the natural ability of the protein monomers to associate.

Tsien et al. (WO97/28261) teach that fluorescent proteins having the proper emission and excitation spectra that are brought into physically close proximity with one another can exhibit fluorescence resonance energy transfer ("FRET"). The invention of WO97/28261 takes advantage of that discovery to provide tandem fluorescent protein constructs in which two fluorescent protein labels capable of exhibiting FRET are coupled through a linker to form a tandem construct. In the assays of the Tsien et al. application, protease activity is monitored using FRET to determine the distance between fluorophores controlled by a peptide linker and subsequent hydrolysis thereof. Other applications rely on a change in the intrinsic fluorescence of the protein as in the kinase assays of WO98/06737.

The present invention instead encompasses the use of detection procedures to monitor the association of polypeptides, as described herein, which are labeled with fluorescent or non-fluorescent labels (protein and chemical). In the invention, FRET, fluorescence correlation spectroscopy, fluorescence anisotropy, fluorescence polarization, monomer:excimer fluorescence, or other techniques indicate the proximity of two polypeptide binding partners. The partners associate either in the presence or absence of a given modification to a binding site on at least one of the binding partner polypeptides, reflecting the modification state of one or both of the binding partners and, consequently, the level of activity of a protein-modifying enzyme.

There is a need in the art for efficient means of monitoring and/or modulating protein modification, including post-translational modification.

SUMMARY OF THE INVENTION

It is an object of the invention to provide methods, compositions, and kits for monitoring activity of one of more enzymes that modify proteins, including post-translational modification. Another object of the invention provides methods for screening for a candidate modulator of enzyme activity, including post-translational enzyme activity. This and other objects of the invention are provided by one or more of the embodiments described below.

One embodiment of the invention provides a method for monitoring activity of one or more enzymes. One or more tagged binding partner polypeptides, one or more binding partner polypeptides, and one or more enzymes that add or remove a moiety to or from said one or more polypeptides or one or more tagged binding partner polypeptides are mixed. The one or more tagged binding partner polypeptides or said one or more binding partner polypeptides comprise one or more sites for the addition or removal of said moiety. The addition or removal of said moiety promotes binding or dissociation of said one or more binding partner polypeptides to or from the corresponding one or more tagged binding partners, under conditions which promote binding or dissociation of said one or more binding partner polypeptides to or from said one or more tagged binding partners. The binding or dissociation is detected and the detection of binding or dissociation as a result of said mixing is indicative of enzyme activity.

The tagged binding partner polypeptides or binding partner polypeptides can be immobilized on a solid support. Both said one or more tagged binding partner polypeptides and said one or more binding partner polypeptides can comprise one or more sites for the addition or removal of a moiety.

The one or more tagged binding partner polypeptides can be tagged with one or more fluorescent molecules and the detecting can comprise monitoring the rate of diffusion of said fluorescent molecule.

The step of detecting binding can further comprise adding one or more detector molecules comprising a first region that associates with said one or more tagged binding partner polypeptides and a second region comprising one or more reporter molecules. The one or more detector molecules can comprise a said first region selected from the group consisting of a coiled-coil, an antigen, an antibody, a single chain antibody, an oligonucleotide, avidin and its analogues and derivatives, and streptavidin, its analogs and derivatives; and wherein said one or more detector molecules comprise a said second region selected from the group consisting of an enzyme, a radioisotope, a radionuclide, a fluorochrome, and a fluorescent protein. The one or more detector molecules can be pre-bound to the one or more tagged binding partner polypeptides.

The one or more tagged binding partner polypeptides can be tagged with one or more radioactive molecules and said detecting can comprise monitoring the presence or absence of radioactivity.

The one or more binding partner polypeptides can also be tagged. Further, one or more binding partner polypeptides and said one or more tagged binding partner polypeptides can be tagged with one or more fluorescent molecules. Detecting can then comprise monitoring the presence or absence of fluorescent resonance energy transfer (FRET).

The one or more sites can comprise a sequence which directs modification by an enzyme selected from the group consisting of a kinase, a phosphatase, a UDP-N-acetylglucosamine-dolichyl-phosphate-N-acetylglucosamine phosphotransferase, an O-GlcNAc transferase, a glycylpeptide-N-tetradecanoyl transferase, a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, and an NAD:Arginine ADP ribosyltransferase.

The site can promote the addition or removal of a chemical moiety selected from the group consisting of a phosphate moiety ($PO_4$), a ubiquitin moiety, a glycosyl moiety, an ADP-ribosyl moiety, a fatty acid moiety, and a sentrin moiety.

The tag can be selected from the group consisting of a coiled-coil, an antigen, an antibody, a single chain antibody, a radioactive amino acid, a fluorescent molecule, a reporter enzyme, and biotin.

The site can be engineered or naturally occurring.

Another embodiment of the invention provides a kit comprising one or more tagged binding partner polypeptides, one or more binding partner polypeptides, and packaging materials. The one or more tagged binding partner polypeptides or said one or more binding partner polypeptides comprise one or more sites for the addition or removal of a moiety. The addition or removal of said moiety promotes binding or dissociation of said one or more binding partner polypeptides to or from the corresponding one or more tagged binding partner polypeptides. The one or more polypeptides and said one or more tagged binding partner polypeptides bind or dissociate in a manner dependent on modification of said site. The tagged binding partner polypeptides or binding partner polypeptides can be immobilized on a solid support.

The kit can further comprise one or more detector molecules comprising a first region that associates with said one or more tagged binding partner polypeptides and a second region comprising one or more reporter molecules. Further, one or more binding partner polypeptides can comprise one or more tags.

Even another embodiment of the invention provides a composition comprising one or more tagged binding partner polypeptides, one or more binding partner polypeptides, and packaging materials. The one or more tagged binding partner polypeptides or one or more binding partner polypeptides comprise one or more sites for the addition or removal of a moiety. The addition or removal of said moiety promotes binding or dissociation of said one or more binding partner polypeptides with the corresponding one or more tagged binding partner polypeptides. The one or more binding partner polypeptides and said one or more tagged binding partner polypeptides bind or dissociate in a manner dependent on modification of said site. The tagged binding partner polypeptides or binding partner polypeptides can be immobilized on a solid support.

The composition can further comprise one or more detector molecules comprising a first region that associates with said one or more tagged binding partner polypeptides and a second region comprising one or more reporter molecules. Further, one or more binding partner polypeptides can comprise one or more tags.

In still another embodiment of the invention a method of screening for a candidate modulator of enzymatic activity is provided. One or more tagged binding partner polypeptides, one or more binding partner polypeptides, and one or more enzymes that adds or removes a moiety to or from said binding partner polypeptide or said one or more tagged binding partner polypeptides are mixed. The one or more tagged binding partner polypeptides or said one or more binding partner polypeptides comprise one or more sites for the addition or removal of said moiety, wherein addition or removal of said moiety promotes binding or dissociation of said one or more binding partner polypeptides to or from the corresponding one or more tagged binding partner polypeptides, under conditions which promote binding of said one or more binding partner polypeptides and said one or more tagged binding partner polypeptides. Binding or dissociation of said one or more binding partner polypeptides to or from said one or more tagged binding partner polypeptides in both the presence and absence of a candidate modulator of enzymatic activity is detected. Where detection of the amount binding or dissociation in the presence of the candidate modulator that is lesser or greater as compared to the amount of binding or dissociation in the absence of the candidate modulator indicates modulation of enzymatic activity by said candidate modulator.

Another embodiment of the invention provides a method for monitoring activity of one or more protease enzymes. One or more tagged binding partner polypeptides, one or more immobilized binding partner polypeptides, and one or more protease enzymes are mixed. One or more tagged binding partner polypeptides or said one or more immobilized binding partner polypeptides are susceptible to protease digestion and protease digestion promotes binding or dissociation of said one or more immobilized binding partner polypeptides with or from the corresponding one or more tagged binding partners. This occurs under conditions which promote binding or dissociation of said one or more immobilized binding partner polypeptides with or from said one or more tagged binding partners. The binding or dissociation is detected, wherein detection of binding or dissociation as a result of said mixing is indicative of protease activity.

The one or more tagged binding partner polypeptides can be tagged with one or more fluorescent molecules and detecting can then comprise monitoring the rate of diffusion of said fluorescent molecule.

The step of detecting binding can further comprise adding one or more detector molecules comprising a first region that associates with said one or more tagged binding partner polypeptides and a second region comprising one or more reporter molecules.

The one or more detector molecules can comprise a said first region selected from the group consisting of a coiled-coil, an antigen, an antibody, a single chain antibody, an oligonucleotide, avidin and its analogues and derivatives, and streptavidin, its analogs and derivatives. The one or more detector molecules can further comprise a second region selected from the group consisting of an enzyme, a radioisotope, a radionuclide, a fluorochrome, and a fluorescent protein.

The one or more detector molecules can be pre-bound to the one or more tagged binding partner polypeptides.

The one or more tagged binding partner polypeptides can be tagged with one or more radioactive molecules and detected by monitoring the presence or absence of radioactivity.

The one or more immobilized binding partner polypeptides can be tagged. Further, one or more immobilized binding partner polypeptides and said one or more tagged binding partner polypeptides can be tagged with one or more fluorescent molecules. The detecting can then comprise monitoring the presence or absence of fluorescent resonance energy transfer (FRET).

Another embodiment of the invention provides a kit comprising one or more tagged binding partner polypeptides, one or more immobilized binding partner polypeptides; and packaging materials. The one or more tagged binding partner polypeptides or said one or more immobilized binding partner polypeptides is susceptible to protease digestion, where protease digestion promotes binding or dissociation of said one or more immobilized binding partner polypeptides with or from the corresponding one or more tagged binding partners under conditions which promote binding or dissociation of said one or more immobilized binding partner polypeptides with said one or more tagged binding partners.

The kit can further comprise one or more detector molecules comprising a first region that associates with said one or more tagged binding partner polypeptides and a second region comprising one or more reporter molecules. Further, one or more immobilized binding partner polypeptides can further comprise one or more tags.

Still another embodiment of the invention provides a composition comprising one or more tagged binding partner polypeptides, one or more immobilized binding partner polypeptides, and packaging materials. The or more tagged binding partner polypeptides or said one or more immobilized binding partner polypeptides is susceptible to protease digestion, wherein said protease digestion promotes binding or dissociation of said one or more immobilized binding partner polypeptides with or from the corresponding one or more tagged binding partners under conditions which promotes binding or dissociation of said one or more immobilized binding partner polypeptides with or from said one or more tagged binding partners.

The composition can further comprise one or more detector molecules comprising a first region that associates with said one or more tagged binding partner polypeptides and a second region comprising one or more reporter molecules. The composition can also comprise one or more binding partner polypeptides further comprising one or more tags.

Another embodiment of the invention provides a method of screening for a candidate modulator of enzymatic activity. One or more tagged binding partner polypeptides, one or more immobilized binding partner polypeptides and one or more protease enzymes are mixed. The one or more tagged binding partner polypeptides or said one or more immobilized binding partner polypeptides are susceptible to protease digestion, wherein said protease digestion promotes binding or dissociation of said one or more immobilized binding partner polypeptides to or from the corresponding one or more tagged binding partners, under conditions which promotes binding or dissociation of said one or more immobilized binding partner polypeptides to said one or more tagged binding partners. Binding or dissociation of said one or more immobilized binding partner polypeptides to said one or more tagged binding partner polypeptides in both the presence and absence of a candidate modulator of protease activity is detected. Detection of the amount binding or dissociation in the presence of the candidate modulator that is lesser or greater as compared to the amount of binding or dissociation in the absence of the candidate modulator indicates modulation of protease activity by said candidate modulator.

As used herein, the term "polypeptide" refers to a polymer in which the monomers are amino acids and are joined together through peptide or disulphide bonds. "Polypeptide" refers to a full-length naturally-occurring amino acid chain or a fragment thereof, such as a selected region of the polypeptide that is of interest in a binding interaction. A polypeptide can also refer to a synthetic amino acid chain or fragment thereof, or a combination of naturally occurring amino acid chains and synthetic amino acid chains. A polypeptide can comprise one or more functional protein domains, such a proteolytic domain or a nucleic acid binding domain. As used herein a fragment is an amino acid sequence that is a portion of a full-length polypeptide, between about 8 and about 500 amino acids in length, preferably between about 8 and about 300 amino acids in length, more preferably about 10 to about 50 or 100 amino acids in length. A peptide is a short amino acid sequence that is between about 10 to about 40 amino acids long, and preferably between about 10 and about 35 amino acids. Unnatural amino acids, for example, β-alanine, phenyl glycine, and homoarginine may be included in the polypeptides, fragments, and peptides of the invention. Commonly-encountered amino acids which are not gene-encoded may also be used in the present invention. All of the amino acids used in the present invention may be either a D- or L- optical isomer. L-isomers are preferred. In addition, other peptidomimetics are also useful, e.g. in linker sequences of polypeptides of the present invention (see Spatola, 1983, in *Chemistry and Biochemistry of Amino Acids, Peptides and Proteins,* Weinstein, ed., Marcel Dekker, New York, p. 267).

As used herein with regard to modification of a polypeptide, the term "site" refers to an amino acid sequence which is recognized by (i.e., a signal for) a modifying enzyme for the purpose of modification (i.e., addition or removal of a "moiety" as defined below, or proteolysis) of the polypeptide or a portion thereof. A "site" additionally refers to the single amino acid which is modified. It is contemplated that a site comprises a small number of amino acids, as few as one but typically from 2 to 10, less often up to 30 amino acids, and further that a site comprises fewer than the total number of amino acids present in the polypeptide.

A "site" for modification may be present on one or both of the binding partners. More than one site for modification can be present on one or both of the binding partners. If such sites are present on both of the binding partners, binding between the binding partners may be dependent upon the modification state of one or both sites. If a single polypeptide chain comprises both binding partners, the state of modification of one or both sites can determine whether binding between the two domains occurs.

As used herein, the term "modification" refers to the addition or removal of a chemical "moiety", as described herein, to or from a site on a polypeptide chain or the proteolytic cleavage of a polypeptide chain.

As used interchangeably herein, the terms "moiety" and "group" refer to one of the post-translationally added or removed groups referred to herein: i.e., one of a phosphate, ubiquitin, glycosyl, fatty acyl, sentrin or ADP-ribosyl moiety.

The terms "addition" or "adds" or "add" when referring to a moiety means the covalent or noncovalent attachment of said moiety to a polypeptide of the invention. The terms "removal" or "remove" or "removes" when referring to a moiety refers to the destruction of a covalent or noncovalent attachment of a moiety from a polypeptide of the invention.

As used herein, the term "binding partner" refers to a polypeptide or fragment thereof that binds to a binding partner comprising a binding domain, sequence, or polypeptide, as defined herein, in a manner which is dependent upon the state of modification of a site for modification which is, at a minimum, present upon the binding domain, sequence, or polypeptide; the binding partner itself may, optionally, comprise such a site and binding between the binding domain, fragment or polypeptide with its corresponding binding partner may, optionally, depend upon modification of that site. A binding partner does not necessarily have to contain a site for modification if such a site is not required to be present on it for modification-dependent association between it and a binding domain, sequence, or polypeptide.

As referred to herein, a polypeptide is "susceptible to digestion by a protease" or "susceptible to proteolytic cleavage" if it is available for cleavage by one or more protease enzymes in accordance with the present invention. Preferably, the polypeptide is susceptible to digestion by a specific protease enzyme, and even more preferably only susceptible to digestion by a specific protease enzyme. This facilitates the reduction of non-specific or background proteolysis.

As used herein, the term "associates" or "binds" refers to a binding partner polypeptide as described herein and its binding partner having a binding constant sufficiently strong to allow detection of binding by detection methods, which are in physical contact with each other and have a dissociation constant (Kd) of about 10 µM or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a discernable change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 µM (Kd). In many cases, the Kd will be in the mM range.

As used herein the term "prevents binding" or "prevents association" or "promotes dissociation" refers to the ability of at least one moiety, such as a ubiquitin moiety, a glycosyl moiety, a phosphate moiety, a fatty acyl moiety, a sentrin moiety, or an ADP-ribosyl moiety, or proteolysis to inhibit the association, as defined above, of binding partners by at least 10%, preferably by 25–50%, highly preferably by 75–90% and, most preferably, by 95–100% relative association observed in the absence of such a modification under the same experimental conditions.

As used herein, the term "promotes binding" or "promotes association" refers to that which causes an increase in binding of the binding domain and its binding partner of at least two-fold, preferably 10- to 20-fold, highly preferably 50- to 100-fold, more preferably from 200- to 1000-fold, and, most preferably, from 200 to 10,000-fold.

The terms "complex", "dimer", "multimer" and "oligomer" as used herein, refer to binding partners in the associated or bound state. More than one molecule of each of the two or more proteins may be present in a complex, dimer, multimer or oligomer according to the methods of the invention.

BRIEF DESCRIPTIONS OF THE DRAWINGS

FIG. 1 presents a schematic of ZAP70-F labeling with J-fluorescein.

FIG. 2 presents fluorescence polarization increase due to binding of fluorescein labeled peptide 1 to ZAP70-FJ.

Figure 7:
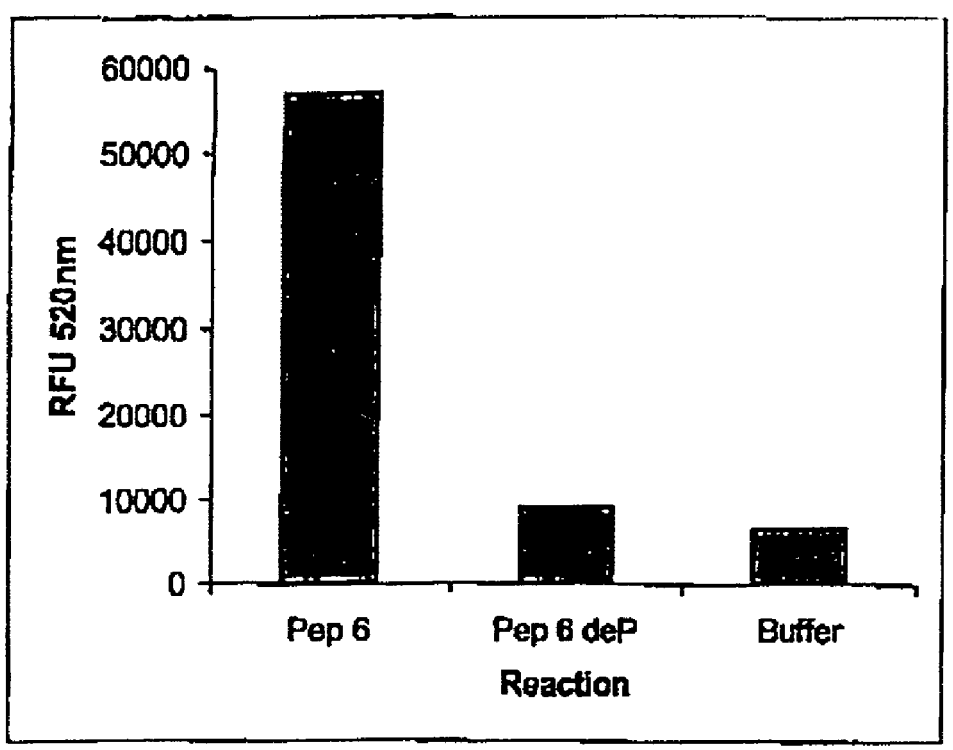

FIG. 7 shows phosphorylated peptide (pep 6) bound to streptavidin coated plate at 2.5 µg/ml in 200 µl PBS containing 0.2% Tween 20 and 1% BSA. Bound peptide treated with YOP phosphatase (6 U) before detecting with an SH2 domain labeled with GFP (2 µM, diluted in TBST/BSA). One hour allowed for binding the peptide at RT. Phosphatase reaction carried out in 100 µl phosphatase buffer (e.g. 25 mM Tris-HCl pH 7.2, 5 mM EDTA 10 mM β-mercaptoethanol, 50 µg/ml BSA) at 37° C. Reaction washed off 3×200 µl PBST/BSA. GFPZAP applied for 1 hour at RT. Excess probe washed off as before and plate read on BMG Polarstar Galaxy, exλ 485 nm, emλ 520 nm.

Figure 8:
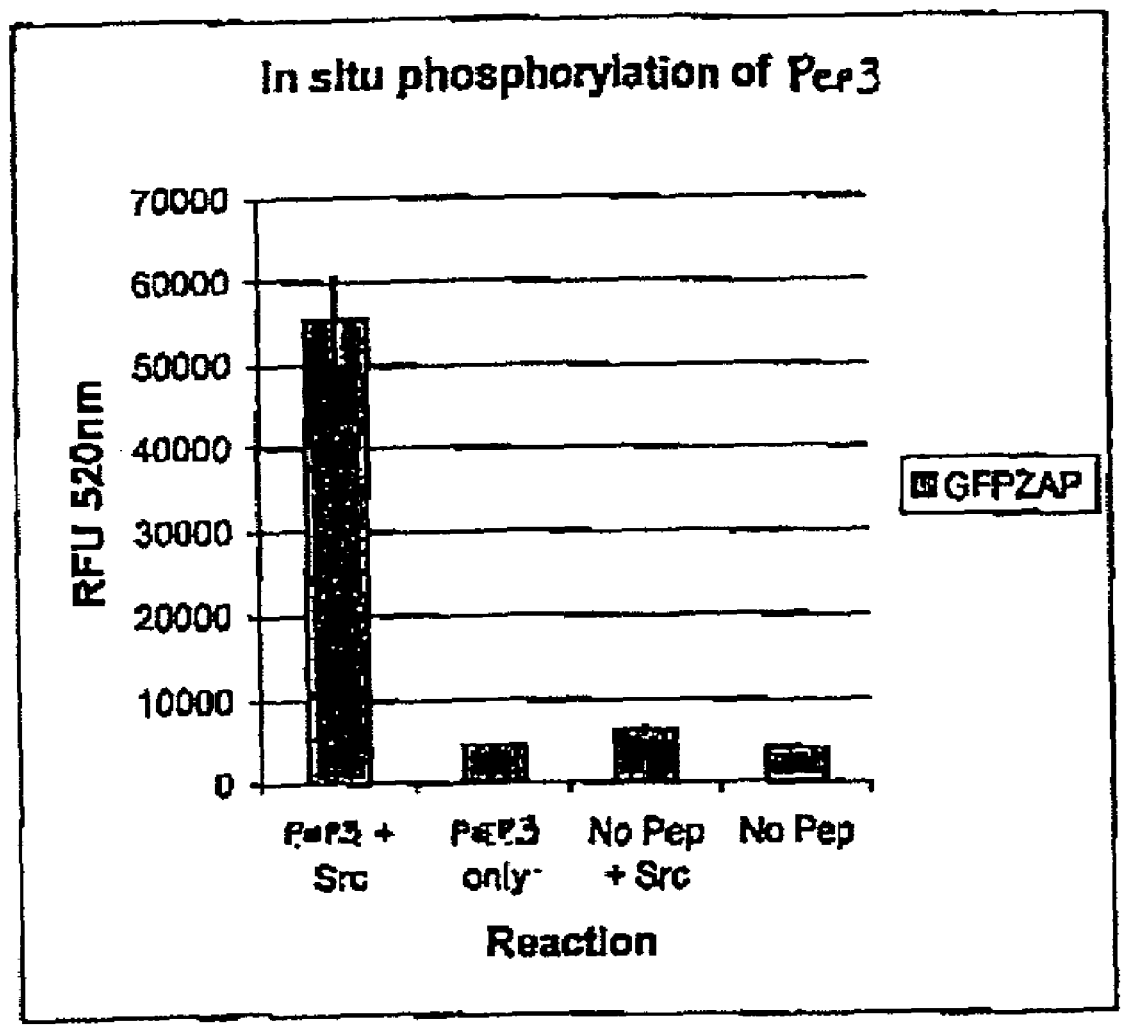

FIG. 8 shows in situ phosphorylation of peptide 3 (unphos) by Src kinase. Peptide bound to streptavidin coated plate at 2.5 µg/ml in 200 µl TBS containing 0.2% Tween 20 and 1% BSA. Plate was then treated with Src kinase (6 U) in Src kinase buffer (e.g. 20 mM Tris-HCl pH 7.2, 1 mM ATP, 10 mM $MgCl_2$, 0.04 mM EDTA, 0.003% (v/v) Brij 35, 0.04mg/ml BSA, 0.08% (v/v) β-mercaptoethanol) for 1 hour at 37° C. Reaction washed off 3×200 µl TBST. Phosphorylation detected by 200 µl GFPZAP constructs applied at 1 µM in TBST/BSA for 1 hour at RT. Excess washed off 6×200 µl TBST.

DETAILED DESCRIPTION

The use of binding partner polypeptides that bind to each other in a modification dependent manner can be exploited for the measurement of the activity of a modification enzyme. For instance, naturally occurring SH2 domains bind to specific tyrosine phosphorylated sequences in a second protein domain. The extent of SH2:pTyr binding is dependent on the action of a protein kinase or protein phosphatase which adds or removes phosphate moieties. This property can be exploited to devise tools for the rapid, quantitative measurement of protein modifying enzymes by measuring the extent of binding of isolated preparations of such domains, in response to incubation with a modification enzyme.

One way to quantitatively measure the effect of a modification enzyme such as a kinase, phosphatase, or protease is to label one or both of the modification dependent binding partner polypeptides with fluorescent labels. The interaction between the binding partners can then be followed in solution using fluorescence resonance energy transfer (FRET) or fluorescence polarization (FP) based assays, where one or both of the partners involved in the interaction are labeled with a fluorophore. Alternatively, immobilized formats can be used, where one binding partner polypeptide is fixed to a solid surface and the binding of a second, fluorescently labeled partner is detected.

Using combinations of different, modification dependent binding partner polypeptides, the activities of several enzymes can be measured simultaneously. This is advantageous for initial phases of the drug discovery process, where rapid assessment of potential drug candidates against a panel of modification enzymes is necessary to detect selectively acting compounds. In solution phase assays, the number of enzymes that can be measured at one time depends on the number of fluorophores able to be simultaneously detected by a suitable instrument. Using immobilized formats, where the different modification dependent binding partner polypeptides can be separated spatially, many fluorophores and consequently many enzyme activities can be detected.

Binding Partner Polypeptides

A binding partner polypeptide comprises a binding domain that is capable of binding to a binding domain of another binding partner polypeptide in a manner which is dependant upon the state of modification of a site for modification which is present on a binding domain of one or both of the binding partner polypeptides. Binding partner polypeptides can be heterodimeric or homodimeric and each binding partner can comprise at least 1, 2, 3, 4, 5, 10, 20, or more binding domains.

A binding domain comprises amino acid residues of a first polypeptide, in a three dimensional sense, that are required for binding between the first polypeptide and its binding partner polypeptide. The amino acids of a binding domain can be either contiguous or non-contiguous. A binding domain must include at least 1 amino acid, and can include 2 or more, preferably 4 or more, and up to 8, 10, 100, 1000, or more amino acids which are contiguous (i.e., covalently linked by peptide bonds) or non-contiguous. A binding domain can exist on a polypeptide that consists solely of binding domain residues or can, instead, be found in the context of a larger polypeptide chain, i.e. one that comprises amino acids other than those of the binding domain. The polypeptide can be either naturally-occurring, i.e., found in nature, or recombinant and, in the case of the latter, can comprise either natural or non-natural amino acid sequences.

A binding domain may be natural or engineered. A naturally occurring binding domain refers to a polypeptide or polynucleotide encoding the polypeptide that can be found in nature. An engineered binding domain is a polypeptide (or a polynucleotide encoding the polypeptide) which is altered (i.e., by insertion, deletion, or substitution of at least one amino acid) such that the binding domain amino acid sequence is no longer as found in nature.

Preferably, a binding partner polypeptide comprising a binding domain is isolated, i.e., a molecule or population of molecules that is substantially pure (free of contaminating molecules of unlike amino acid sequences). A binding partner polypeptide can be a full-length amino acid chain or a fragment or peptide thereof, such as a selected region of the polypeptide that is of interest in a binding assay and for which a binding partner is known or determinable.

A binding partner polypeptide comprising a binding domain can occur in a single- or double chain format. In a double chain format, a polypeptide comprising a binding domain is a different polypeptide chain from that comprising or consisting of its binding partner and is not otherwise covalently linked to it. In single chain format, a polypeptide comprising a binding domain is covalently linked to its binding partner, either through an intervening amino acid sequence or a chemical linker.

Preferably, a binding partner polypeptide is produced recombinantly. A polynucleotide encoding a binding partner polypeptide of the invention can be introduced into an expression vector which can be expressed in a suitable expression system. A variety of bacterial, yeast, mammalian, and insect expression systems are available in the art and any such expression system can be used. Binding partner polypeptides can be produced as a fusion protein, which comprises two or more protein segments. One protein segment of a fusion protein comprises a binding partner polypeptide. This protein segment is fused to one or more protein segments by means of peptide bonds. The additional protein segment or segments can comprise another binding partner, or a tag, such as an antigen, coiled-coil region, a reporter enzyme, and a biotinylation peptide. Alternatively, the additional protein segment or segments can be a detectable marker, a signal sequence, a linker, or a ligand useful in protein purification, such as glutathione-S-transferase and staphylococcal protein A. Techniques for making fusion proteins, either recombinantly or by covalently linking two or more protein segments, are well known in the art.

Optionally, a binding partner polypeptide of the invention can be produced by translation in a cell-free translation system or can be constructed by solid phase protein synthesis. Such methods are well known in the art. A binding partner polypeptide can also be isolated from bacteria, yeast, insect, or mammalian cells using, for example, affinity purification.

Modification Site

A binding domain of a binding partner polypeptide can comprise a site for modification-dependant binding to a binding partner. At least one binding partner of a binding partner pair comprises a site for polypeptide modification. A site for modification can be natural or engineered and comprises an amino acid sequence which is recognized by (i.e., a signal for) a modifying enzyme for the purpose of modification (i.e., addition or removal of a moiety or proteolysis) of a polypeptide or a portion thereof. A site can be a single amino acid which is modified. It is contemplated that a site comprises a small number of amino acids, as few as one but typically from 2 to 10, less often up to 30 amino acids. Preferably, a site comprises fewer than the total number of amino acids present in the polypeptide. The state of modification of a site will determine whether binding between a binding domain of a polypeptide and a binding partner occurs.

Post-translational Protein Modifications

ADP-ribosylation

Mono-ADP-ribosylation is a post-translational modification of a protein which likely plays a fundamental role in cellular signaling. A number of mono-ADP-ribosyl-transferases have been identified, including endogenous enzymes from both bacterial and eukaryotic sources and bacterial toxins. For example, NAD:Arginine ADP ribosyltransferase is a mono-ADP-ribosylating enzyme, that uses the protein to be modified and nicotinamide adenine dinucleotide (NAD+) as substrates (Zolkiewska et al., (1992) *Proc. Natl. Acad. Sci. U.S.A.*, 89:11352). The reactions catalyzed by bacterial toxins such as cholera and pertussis toxin result in the permanent modification of heterotrimeric G proteins. Endogenous transferases are also thought to modify G proteins and therefore to play a role in signal transduction in the cell (de Murcia et al., (1995) *Trends Cell Biol.*, 5:78).

The extent of the effects that ADP-ribosylation can mediate in the cell is illustrated by the example of brefeldin A, a fungal toxin metabolite of palmitic acid. This toxin induces the mono-ADP-ribosylation of BARS-50 (a G protein involved in membrane transport) and glyceraldehyde-3-phosphate dehydrogenase. The cellular effects of brefeldin A include the blocking of constitutive protein secretion and the extensive disruption of the Golgi apparatus. Inhibitors of the brefeldin A mono-ADP-ribosyl-transferase reaction have been shown to antagonize the disassembly of the Golgi apparatus induced by the toxin (Weigert et al., (1997) *J. Biol. Chem.*, 272:14200). A number of amino acid residues within proteins have been shown to function as ADP-ribose acceptors. Bacterial transferases have been identified which modify arginine, asparagine, cysteine and diphthamide residues in target proteins. Endogenous eukaryotic transferases are known which also modify these amino acids, in addition there is evidence that serine, threonine, tyrosine, hydroxyproline, and histidine residues may act as ADP-ribose acceptors but the relevant transferases have not yet been identified (Cervantes-Laurean et al., (1997) *Methods Enzymol.*, 280:275 and references therein).

Poly-ADP-ribosylation is thought to play an important role in events such as DNA repair, replication, recombination and packaging and also in chromosome decondensation. The enzyme responsible for the poly-ADP-ribosylation of proteins involved in these processes is poly (ADP-ribose) polymerase (PARP; for *Drosophila melanogaster* PARP, see Genbank Accession Nos. D13806, D13807, and D13808). The discovery of a leucine zipper in the self-poly(ADP-ribosyl)ation domain of the mammalian PARP (Uchida et al., (1993) *Proc. Natl. Acad. Sci. U.S.A.*, 90:3481) suggested that this region may be important for the dimerization of PARP and also its interaction with other proteins (Mendoza-Alvarez et al., (1993) *J. Biol. Chem.*, 268:22575).

Specific examples of ADP-ribosylation sites are those found at $Cys_3$ and $Cys_4$ (underlined) of the B-50 protein (Coggins et al., (1993) *J. Neurochem.*, 60:368; SwissProt Accession No. P06836):

MLCCMRRTKQVEKNDDD (SEQ ID NO:1)

and Pγ (the γ subunit of cyclic GMP phophodiesterase; Bondarenko et al., (1997) *J. Biol. Chem.*, 272:15856; Genbank Accession No. X04270):

FKQRQTRQFK (SEQ ID NO:2)

Ubiquitination

Ubiquitination of a protein targets the protein for destruction by the proteosome. This process of destruction is very rapid ($t_{1/2}$~60 seconds), and many proteins with rapid turnover kinetics are destroyed by this route. These include cyclins, p53, transcription factors, and transcription regulatory factors, among others. Thus, ubiquitination is important in processes such as cell cycle control, cell growth, inflammation, signal transduction; in addition, failure to ubiquitinate proteins in an appropriate manner is implicated in malignant transformation. Ubiquitin is a 76-amino-acid protein which is covalently attached to a target protein by an isopeptide bond, between the ε-amino group of a lysine residue and the C-terminal glycine residue of ubiquitin. Such modification is known as mono-ubiquitination, and this can occur on multiple Lys residues within a target protein. Once attached, ubiquitin can itself be ubiquitinated, thus forming extended branched chains of polyubiquitin. It is this latter state which signals destruction of the target protein by the proteosome. In the process of destruction, it appears that the polyubiquitinated protein is taken to the proteosome via a molecular chaperone protein, the ubiquitin molecules are removed undamaged (and recycled), and the target is degraded.

Ubiquitination is a complex process, which requires the action of three enzymes: ubiquitin activating enzyme E1 (for human, Genbank Accession No. X56976), ubiquitin conjugating enzyme E2, also referred to as the ubiquitin carrier protein, (for human 17 kDa form, Genbank Accession No. X78140), and ubiquitin protein ligase E3α (UBR1; human, Genbank Accession No. AF061556). There are multiple forms of each of these enzymes in the cell, and the above examples are, therefore, non-limiting.

The signals contained within a protein which determine whether the protein is subject to the process of ubiquitination and destruction are two-fold: first, the identity of the N-terminal amino acid (so called N-end rule, Varshavsky, (1996) *Proc. Natl. Acad. Sci. U.S.A.*, 93:12142), and secondly the presence of a suitably positioned Lys residue in the protein (Varshavsky, (1996)). This Lys can be up to ~30 amino acids away from the N-terminus in experimental examples studied where the N-terminus is a flexible, poorly-structured element of the protein (Varshavsky, (1996)) or could potentially be anywhere in the sequence where this presents it at an appropriate location relative to the N-terminus. An appropriate location is one which allows interaction of both the N-terminal residue and this integral lysine with the enzyme(s) responsible for ubiquitination, presumably simultaneously. The Lys residue becomes ubiquitinated, and the process of destruction is initiated. N-terminal residues can be classed as stabilizing (s) or destabilizing (d), and the inclusion of an amino acid in one of these broad classes is species-dependent (prokaryotes differ from yeast, which differs from mammals). Varshavsky, (1996).

In a dimeric (or other oligomeric) protein the destabilizing N-terminal residue and the internal Lys can be in cis (on a single peptide), but may also be in trans (on two different polypeptides). The trans-recognition event will only take place while the complex is physically associated. Only the ubiquitinated subunit is proteolyzed. Varsharsky, (1996).

Two examples of ubiquitination sites from natural proteins, IκB (Dai et al., (1998) *J. Biol. Chem*, 273:3562; Genbank Accession No. M69043) and β-galactosidase (Johnson et al., (1990) *Nature*, 346:287) are as follows:

IκB NH$_3$-MFQAAERPQEWAMEGPRDGL
KKERLLDDRH-COOH (SEQ ID NO:3)

β-galactosidase NH$_3$-HGSGAWLLPVSLVKR
KTTLAP-COOH (SEQ ID NO:4).

The ubiquitinated lysine residue is underlined for each (e.g., $Lys_{15}$ and $Lys_{17}$ for β-galactosidase).

According to the invention, a ubiquitination assay measures the addition of ubiquitin to a binding domain.

Glycosylation

N-linked glycosylation is a post-translational modification of proteins which occurs in the endoplasmic reticulum and Golgi apparatus and is utilized with some proteins en route for secretion or destined for expression on the cell surface or in another organelle. A carbohydrate moiety is attached to Asn residues in the non-cytoplasmic domains of target proteins, and the consensus sequence for a glycosylation site is:

NxS/T, (SEQ ID NO:29)

where x cannot be proline or aspartic acid. Shakineshleman, (1996) *Trends Glycosci. Glycotech.*, 8:115. N-linked sugars have a common five-residue core consisting of two GlcNAc residues and three mannose residues due to the biosynthetic pathway. This core is modified by a variety of Golgi enzymes to give three general classes of carbohydrates known as oligomannosyl, hybrid and lactosamine-containing or complex structures (Zubay, (1998) *Biochemistry*, Wm. C. Brown Publishers). An enzyme known to mediate N-glycosylation at the initial step of synthesis of dolichyl-P-P-oligosaccharides is UDP-N-Acetylglucosamine-Dolichyl-phosphate-N-acetylsglucosamine phosphotransferase (for mouse, Genbank Accession Nos. X65603 and S41875).

Oxygen-linked glycosylation also occurs in nature with the attachment of various sugar moieties to Ser or Thr residues (Hansen et al., (1995) *Biochem. J.*, 308:801). Intracellular proteins are among the targets for O-glycosylation through the dynamic attachment and removal of O-N-Acetyl-D-glucosamine (O-GlcNAc; reviewed by Hart, (1997) *Ann. Rev. Biochem.*, 66:315). Proteins known to be O-glycosylated include cytoskeletal proteins, transcription factors, the nuclear pore protein complex, and tumor-suppressor proteins (Hart, (1997)). Frequently these proteins are also phosphoproteins, and there is a suggestion that O-GlcNAc and phosphorylation of a protein play reciprocal roles. Furthermore, it has been proposed that the glycosylation of an individual protein regulates protein:protein interactions in which it is involved.

Specific sites for the addition of O-GlcNAc are found, for example, at $Ser_{277}$, $Ser_{316}$ and $Ser_{383}$ of $p67^{SRF}$ (Reason et al., (1992) *J. Biol. Chem.*, 267:16911; Genbank Accession No. J03161). The recognition sequences encompassing these residues are shown below:

```
274GTTSTIQTAP              (SEQ ID NO:5)

313SAVSSADGTVLK            (SEQ ID NO:6)

374DSSTDLTQTSSSGTVTLP      (SEQ ID NO:7).
```

The identity of sites of O-GlcNAc is additionally known for a small number of proteins including c-myc ($Thr_{58}$, also a phosphorylation site; Chou et al., (1995) *J. Biol. Chem.*, 270:18961), the nucleopore protein p62 (see Reason et al., (1992)):

MAGGPADTSDPL (SEQ ID NO:8)

and band 4.1 of the erythrocyte (see Reason et al., (1992)):

AQTITSETPSSTT (SEQ ID NO:9).

The site at which modification occurs is, in each case, underlined. The reaction is mediated by O-GlcNAc transferase (Kreppel et al., (1997) *J. Biol. Chem.*, 272:9308). These sequences are rich in helix breaking residues (e.g., G and P) and may be difficult to incorporate into a helical framework.

Prenylation (Fatty Acylation)

The post-translational modification of proteins with fatty acids includes the attachment of myristic acid to the primary amino group of an N-terminal glycine residue (Johnson et al., (1994) *Ann. Rev. Biochem.*, 63:869) and the attachment of palmitic acid to cysteine residues (Milligan et al., (1995) *Trends Biochem. Sci.*, 20:181).

Fatty acylation of proteins is a dynamic post-translational modification which is critical for the biological activity of many proteins, as well as their interactions with other proteins and with membranes. Thus, for a large number of proteins, the location of the protein within a cell can be controlled by its state of prenylation (fatty acid modification) as can its ability to interact with effector enzymes (ras and MAP kinase, Itoh et al., (1993) *J. Biol. Chem.*, 268: 3025; ras and adenylate cyclase (in yeast; Horiuchi et al., (1992) *Mol. Cell. Biol.*, 12:4515) or with regulatory proteins (Shirataki et al., (1991) *J. Biol. Chem.*, 266:20672). The prenylation status of ras is important for its oncogenic properties (Cox, (1995) *Methods Enzymol.*, 250:105) thus interference with the prenylation status of ras is considered a valuable anti-cancer strategy (Hancock, (1993) *Curr. Biol.*, 3:770).

Sentrinization

Sentrin is a novel 101-amino acid protein which has 18% identity and 48% similarity with human ubiquitin (Okura et al., (1996) *J. Immunol.*, 157:4277). This protein is known by a number of other names including SUMO-1, UBL1, PIC1, GMP1, and SMT3C and is one of a number of ubiquitin-like proteins that have recently been identified. Sentrin is expressed in all tissues (as shown by Northern blot analysis), but mRNA levels are higher in the heart, skeletal muscle, testis, ovary, and thymus.

The sentrinization of proteins is thought to involve the ubiquitin-conjugating enzyme Ubc9 (Gong et al., (1997) *J. Biol. Chem.*, 272:28198). The interaction between these two proteins in the yeast two-hybrid screen is very specific, suggesting that this is a biologically relevant phenomenon. The interaction is dependent upon the presence of the conserved C-terminal Gly-Gly residues present in sentrin (Gong et al., (1997)). The conjugation of sentrin to other proteins via $Gly_{97}$ requires the cleavage of the C-terminal four amino acids of the protein, His-Ser-Thr-Val (SEQ ID NO:30).

One important protein shown to be modified by the addition of sentrin is the Ran-specific GTPase-activating protein, RanGAP1, which is involved in nuclear import of proteins bearing nuclear-localization signals (Johnson and Hochstrasser, (1997) *Trends Cell Biol.*, 7:408). Conjugation of RanGAP1 and sentrin is essential both for the targeting of RanGAP1 to its binding partner on the nuclear pore complex (NPC) and for the nuclear import of proteins. Sentrin itself does not bind with high affinity to the NPC and it is, therefore, likely that it either provokes a conformational change in RanGAP1 that exposes a binding site or, alternatively, that the binding site is formed using both sentrin and RanGAP1 sequences. There is evidence to suggest that the conjugation of sentrin to RanGAP1 is necessary for the formation of other sentrinized proteins (Kamitani et al., (1997) *J. Biol. Chem.*, 272:14001) and that the majority of these sentrinized proteins are found in the nucleus.

Sentrin has been shown in yeast two-hybrid screens to interact with a number of other proteins, including the death domains of Fas/APO1 and the TNF receptors, PML, RAD51, and RAD52 (Johnson and Hochstrasser, (1997)). These interactions implicate sentrin in a number of important processes. Fas/APO1 and TNF receptors are involved in transducing the apoptosis signal via their death domains. Ligation of Fas on the cell surface results in the formation of a complex via death domains and death-effector domains, triggering the induction of apoptosis. The overexpression of sentrin protects cells from both anti-Fas/APO and TNF-induced cell death (Okura et al., (1996)). It is not clear whether this protection is achieved simply by preventing the binding of other proteins to these death domains or whether a more complex process is involved, possibly one involving the ubiquitin pathway.

The interaction of sentrin with PML (a RING finger protein) is important, as it points to a disease state in which this protein may play a role. In normal myeloid cells, PML is found in a nuclear multiprotein complex known as a nuclear body. These nuclear bodies are disrupted in acute promyelocytic leukemia, where a chromosomal translocation generates a fusion between regions of the retinoic acid receptor a and PML. This disruption can be reversed by treatment with retinoic acid. It has been shown that PML is covalently modified at multiple sites by members of the sentrin family of proteins (but not by ubiquitin or NEDD8). Two forms of the aberrant fusion protein have been identified, neither of which is modified by sentrin. It is, therefore, thought that differential sentrinization of the normal and aberrant forms of PML may be important in the processes underlying acute promyelocytic leukemia and may help in the understanding of the biological role of the PML protein (Kamitani et al., (1998) *J. Biol. Chem.*, 273:3117).

Phosphorylation

Phosphorylation results from the addition of a phosphate group to a polypeptide, usually to the hydroxyl group of serine, tyrosine, or threonine. A kinase enzyme is capable of adding a phosphate group to a polypeptide and a phosphatase enzyme is capable of removing a phosphate group from a polypeptide. An example is the YOP phosphatase from *Yersinia pestis*.

Sites for post-translational modification may be selected according to the specificity of the enzyme or enzymes to be assayed. Non-limiting examples of sites for phosphorylation/dephosphorylation post-translational modification are shown in Table 1.

TABLE 1

| Kinase | Consensus Sequence | GenBank No./Reference |
|---|---|---|
| cAMP-dependent protein kinase | -RRXRRXS/T- (SEQ ID NO:10) | Cα subunit M34181 RIIβ subunit M31158 |
| Myosin Heavy Chain kinase | -KXXSX- (SEQ ID NO:11) | Trends in Biochem. Sci. (1990) 15:342–346. |
| Myosin Heavy Chain kinase | -RXT- (SEQ ID NO:12) | M93393 |
| Calmodulin-Dependent protein kinase II | -RXXSX- (SEQ ID NO:13) | α chain J02942 β chain M16112 δ chain J05072 γ chain J04063 |
| cGMP-dependent protein kinase | -XSRX- (SEQ ID NO:14) | β isozyme Y07512 |
| Protein kinase C | -XRXXSXRX- (SEQ ID NO:15) | Trends in Biochem. Sci. (1990) 15:342–346. |
| S6 kinase II | -XRXXSX- (SEQ ID NO:16) | α2 isozyme L07599, L07601 |
| dsRNS kinase pp68 | -SELSRR- (SEQ ID NO:17) | Trends in Biochem. Sci. (1990) 15:342–346. |
| Casein kinase I | -XSXXSX- (SEQ ID NO:18) | α isoform X80693 |
| Mammary gland casein kinase | -XSXEX- (SEQ ID NO:19) | Trends in Biochem. Sci. (1990) 15:342–346. |
| Glycogen synthase kinase 3 | -XSXXXSX- (SEQ ID NO:20) | α isoform L40027 |

X signifies any amino acid.
Consensus sequences are taken from Trends Biochem. Sci. (1990) 15:342.
Further examples are tabulated in Pearson and Kemp, (1991) Methods Enzymol. , 200:62.

Non-limiting examples of sites for the addition/removal of other chemical moieties are shown in Table 2.

TABLE 2

| Modification | Protein Source | Consensus Sequence/ Sequence | Reference/ GenBank No. |
|---|---|---|---|
| | | Modified residues indicated in bold. Residues forming part of the recognition site are shown in italics. | |
| ADP-Ribosylation | B-50 | ¹MLCCMRRT*KQVEKND*DD (SEQ ID NO:1) | Coggins et al., 1993, J. Neurochem. , 60:368–71 |
| | γ subunit of cGMP phosphodiesterase | ³⁰FKQRQTRQFK (SEQ ID NO:2) | X04270 |
| Ubiquitination | IκB | ¹MFQAAERPQEWAMEGPRDGLKKERLLDDRH (SEQ ID NO:3) | M69043 |
| | β-Galactosidase | ¹HGSGAWLLPVSLVKR*KTTLAP* (SEQ ID NO:4) | Johnson et al., 1990, Nature , 346:287–291 |
| N-Myristoylation | Src | ¹G*SSKS*KPKD (SEQ ID NO:21) | Resh, 1994, Cell , 76: 411–413 |
| | Lyn | ¹G*CTKS*KRKD (SEQ ID NO:22) | Resh, 1994, supra |

TABLE 2-continued

| Modification | Protein Source | Consensus Sequence/ Sequence | Reference/ GenBank No. |
|---|---|---|---|
| | Yes | $^1$GCIKSKEDK (SEQ ID NO:23) | Resh, 1994, supra |
| | Fyn | $^1$GCVQCKDKE (SEQ ID NO:24) | Resh, 1994, supra |
| | Gα | $^1$GCTLSAEDK (SEQ ID NO:25) | Resh, 1994, supra |
| Palmitylation | Lyn | $^1$GCIKSKRKD (SEQ ID NO:26) | M64608 |
| | Fyn | $^1$GCVQCKDKE (SEQ ID NO:27) | M14676 |
| | Gαi2 | $^1$GCTLSAEDK (SEQ ID NO:28) | Milligan et al., 1995, Trends Biochem. Sci., 20:181–186 |
| N-Glycosylation | | -NXS/T- X can be any amino acid except P (SEQ ID NO:29) | Shakineshleman, 1996, Trends in Glycoscience and Glycotechnology, 8: 115–130 |
| O-Glycosylation | p67$^{SRF}$ | $^{274}$GTTSTIQTAP (SEQ ID NO:5) $^{313}$SAVSSADGTVLK (SEQ ID NO:6) $^{374}$DSSTDLTQTSSSGTVTLP (SEQ ID NO:7) | J03161 |
| Sentrinization | RanGAP1 | | Johnson and Hochstrasser, 1997, Trends Cell Biol., 7: 408–413 |
| | PML | | Kamitani et al., 1998, J. Biol. Chem., 273: 3117–3120 |

Proteolysis

Proteolysis has long been recognised as an important intra- and extracellular modification of proteins. Endopeptidase enzymes recognize particular primary sequence signals (and sometimes also secondary or tertiary structural cues) within a substrate protein and cleave the peptide bond following a particular amino acid. Expopeptidases, on the other hand, digest polypeptides from the N or C terminus. Exopeptidases are generally not sequence-specific. These enzymes play a role in, for example, digestion, the coagulation of blood, the complement cascade and the destruction of inactive, mutated, or foreign forms of proteins in the cell. Proteolysis is also important as a method of recycling amino acids within the cell for the synthesis of new proteins or for utilization as a fuel source. More recently, the role of proteolysis in signalling and in specific intracellular processes has been recognised.

It is clear that aberrant proteolysis plays a significant role in a number of disease processes. Examples include the processing of β-amyloid precursor protein (inappropriate processing of this protein is thought to play a role in Alzheimer's disease), the inappropriate activation of proteolytic enzymes of digestion leading to pancreatitis and a loss of proteolysis of the insulin receptor precursor leading to diabetes. Proteolysis is now understood to play important roles both within the cell and in processes important in homeostasis in multi-cellular organisms. These include:

1. Production of bioactive molecules from inactive precursors. A hallmark of proteolytic enzymes is their production in many cases as inactive proenzymes and their subsequent rapid activation by a proteolytic event. This may be an autocatalytic process or part of a cascade. This is exemplified by the blood clotting cascade and also the cleavage of digestive proproteases to their active form. One of the central events in acute pancreatitis is the premature proteolysis and activation of pancreatic enzymes (especially trypsin) leading to autodigestion of pancreatic tissue amongst other effects (Mergener & Baillie, *Brit. Med. J.* (1998) 316:44). Proteases are also known to activate other proenzymes and to play a role in the generation of other bioactive molecules. An important clinical example of this is the generation of angiotensin II by the enzyme angiotensin converting enzyme (ACE). ACE cleaves the C-terminal two residues from the inactive angiotensin I to produce the active form, angiotensin II. Angiotensin II has potent vasoconstrictive and salt-retentive properties, the control of ACE activity by ACE inhibitors has an important clinical role in the treatment of hypertension, heart failure, myocardial infarction and diabetic nephropathy (Brown & Vaughan, *Circulation* (1998) 97:1411).

2. Destruction of bioactive molecules. An important aspect of a regulatory process is the presence not only of an 'on switch' but also the potential to switch it off again. This is an area in which proteolysis is particularly important as it is an irreversible modification. The only way in which the process can be restarted is by a resynthesis of the destroyed component. This affords a high level of control over timing. An important clinical example of this is the degradation of bradykinin by ACE. Bradykinin has a number of effects in the body including inducing smooth muscle contraction, increasing vascular permeability and promoting vasodilation and natriuresis. This, together with the example above, indicates that ACE is important in the regulation of the balance between the antagonistic effects of angiotensin II and bradykinin (Brown & Vaughan, *Circulation* (1998) 97:1411–1420).

3. Protein turnover. The ability of the cell to degrade unwanted, damaged or foreign proteins is of great importance in the maintenance of the cell. Limited proteolysis of foreign proteins is also important in the antigen presentation process and therefore in an appropriate immune response to pathogens.

4. Post-translational modification. The proteolysis of certain proteins is key in their ability to perform their function in the cell. For example, the biosynthesis of the insulin receptor involves the cleavage of a large precursor to produce the subunits of the receptor complex (Hedo, *J. Biolog. Chem.* (1983) 258:10020). The assembly of the plant lectin concanavalin A (con A) also involves the proteolysis of a precursor protein and the religation of fragments in an altered order to generate the mature protein (Bowles & Pappin, (1988) *Trends Biochem. Sci.* 13:60).

5. A process coincident with other forms of post-translational modification. Proteolysis is an important feature of the processes leading to the addition of glycosylphosphatidylinositol (GPI) anchors to proteins and also in some fatty acylation reactions (such as farnesylation or geranylgeranylation).

Thus, proteolysis is an important post-translational modification of proteins and peptides which occurs both within and outside of the cell and can be an essential part of other forms of post-translational modification such as addition of a GPI anchor or some fatty acids. The ability to measure the cleavage of a protein or peptide at a specific site where that protein or peptide is also accessible for the addition of a prenyl moiety or a GPI anchor will allow the in vitro and in vivo study of processes for which the methods currently available are limited.

According to the invention, one or more of binding partner polypeptides can be susceptible to digestion by a protease enzyme. As noted above, susceptibility to digestion indicates that the polypeptide can be subjected to proteolytic degradation under the appropriate conditions, which in a preferred embodiment means that the polypeptide is cleaved by a protease at a recognition site for the protease enzyme. Alternatively, however, the polypeptide can be susceptible to digestion by an exoprotease, from the N or C terminus. Peptides may be rendered susceptible to protease digestion by inclusion within the peptide sequence of a recognition site for a protease. This may be performed using peptide synthesis techniques well known in the art.

Binding partner polypeptides are preferably constructed so that the protease cleavable site is positioned such that cleavage thereof disrupts or promotes binding of a binding partner polypeptide to its corresponding partner. Preferably, a protease does not cleave a polypeptide in such a manner such that the tag becomes detached therefrom. Location of the protease cleavable site may be determined empirically. As a guide, however, the site should be placed within or proximal to the binding domain which is responsible for the binding of the polypeptide.

The cleavage sites of a number of proteases are known in the art, and set forth in Table 3.

TABLE 3

| Protease | Cut Site(s) | Possible/Proven Role |
|---|---|---|
| Aminopeptidase M | Hydrolysis from free N-terminus | digestion |
| Carboxypeptidase P | Hydrolysis from C-terminus | digestion |

TABLE 3-continued

| Protease | Cut Site(s) | Possible/Proven Role |
|---|---|---|
| Carboxypeptidase Y | Hydrolysis from C-terminus | digestion |
| Caspase 1, 4, 5 | W/LEHD-X[#] (SEQ ID NO:48) | mediator of apoptosis |
| Caspase 2, 3, 7 | DEXD-X[#] (SEQ ID NO:49) | mediator of apoptosis |
| Caspase 6, 8, 9 | L/VEXD-X[#] (SEQ ID NO:50) | mediator of apoptosis |
| Chymotrypsin | Y-X, F-X, T-X, (L-X, M-X, A-X, E-X) | digestion |
| Factor Xa | IEGR-X (SEQ ID NO:51) | blood clotting cascade |
| Pepsin | F-Z, M-Z, L-Z, W-Z (where Z is a hydrophobic residue) but will cleave others | digestion |
| TEV | E(N)XYXQ-S/G[−](SEQ ID NO:52) | polyprotein processing/as a reagent |
| Thrombin | R-X | blood clotting cascade |
| Trypsin | R-X, K-X | digestion |

[#]Ideal cut sites identified by Thornberry et al., (1997) J. Biol. Chem. 272 17907.
[−]Parks et al., (1994) Analytical Biochem. 216:413; Life Technologies Ltd.

The foregoing, or other sites may be engineered into or close to the binding domains of polypeptides according to the invention.

Enzymes

The invention requires the presence of a modifying enzyme which catalyzes either the addition or removal of a modifying group (moiety) or proteolysis. Preferably, the enzyme is one of the following enzymes: a protein phosphatase, a protein kinase, a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase), an NAD:Arginine ADP ribosyltransferase, and a protease. A range of kinases, phosphatases, and other modifying enzymes are available commercially (e.g. from Sigma, St. Louis, Mo.; Promega, Madison, Wis.; Boehringer Mannheim Biochemicals, Indianapolis, Ind.; New England Biolabs, Beverly, Mass.; and others). Alternatively, such enzymes may be prepared in the laboratory by methods well known in the art.

For example, the catalytic sub-unit of protein kinase A (c-PKA) can be purified from natural sources (e.g. bovine heart) or from cells or organisms engineered to heterologously express the enzyme. Other isoforms of this enzyme may be obtained by these procedures. Purification is performed as previously described from bovine heart (Peters et al.,(1977) *Biochem.*, 16:569) or from a heterologous source (Tsien et al., WO92/00388).

The purification of recombinant c-PKA can be done as described in WO 92/00388. General methods of preparing pure and partially-purified recombinant proteins, as well as crude cellular extracts comprising such proteins, are well known in the art. Molecular methods useful in the production of recombinant proteins, such as the enzymes to be assayed according to the invention are well known in the art (for methods of cloning, expression of cloned genes and protein purification, see Sambrook et al., 1989, *Molecular Cloning. A Laboratory Manual.*, 2nd Edition, Cold Spring Harbor Laboratory Press, Cold Spring Harbor, N.Y.; Ausubel et al., *Current Protocols in Molecular Biology*, copyright 1987–1994, Current Protocols, copyright 1994–1998, John Wiley & Sons, Inc.). The sequences of the catalytic subunit of several PKA molecules are found in the Genbank database (see PKA Cα, bovine, Genbank Accession Nos. X67154 and S49260; PKA Cβ1, bovine, Genbank Accession No. J02647; PKA Cβ2, bovine, M60482, the form most likely purified from bovine heart by the protocol disclosed above).

According to the invention, assays of the activity of protein-modifying enzymes can be performed using crude cellular extracts, whether to test the activity of a recombinant enzyme or one which is found in nature, such as in a biological sample obtained from a test cell line or animal or from a clinical patient. In the former case, use of a crude cell extract enables rapid screening of many samples, which potentially finds special application in high-throughput screening methods, e.g. of candidate modulators of protein-modifying enzyme activity. In the latter case, use of a crude extract with compositions and assays of the invention facilitates easy and rapid assessment of the activity of an enzyme of interest in a diagnostic procedure, e.g., one which is directed at determining whether a protein-modifying enzyme is active at a physiologically-appropriate level, or in a procedure designed to assess the efficacy of a therapy aimed at modulating the activity of a particular enzyme.

Table 4 in a non-limiting list of enzymes which perform modifications useful in the invention.

TABLE 4

| Modification | Enzyme | Specific Action | GenBank No./ Reference |
| --- | --- | --- | --- |
| Mono-ADP-Ribosylation | NAD:ArginineADP-ribosyl transferase | | Zolkiewska et al., (1992) PNAS 89:11352. |
| Poly-ADP-Ribosylation | Drosophila PARP (poly (ADP-ribose) polymerase | | D13806, D13807, D13808 |
| Ubiquitination | E1 E2(UBC8) E3(RSP5) | Ubiquitination of large subunit of RNA pol II (Rpb 1) (NB, E2 and E3 confer substrate specificity on the ubiquitination) | X55386, X56507 M65083 U18916, L11119, L11120, U00092, U75972 |
| N-Myristoylation | Glycylpeptide-N-tetradecanoyltransferase (peptide N-myristoyltransferase) | | M86707 |
| N-Glycosylation | UDP-N-acetylglucosamine-dolichyl-phosphate N-acetylglucosamine phosphotransferase | Initial step in synthesis of dolichol-P-P-oligosacharides | X65603, S41875 |
| O-Glycosylation | O-GlcNAc transferase | | Kreppel et al., (1997) J. Biol. Chem. , 272: 9308. |
| Sentrinization | Ubc9 | | Gong et al., (1997) J. Biol. Chem. , 272: 28198. |

Proteases of the invention can be purified from natural sources or from cells or organisms engineered to heterologously express the enzymes. All enzymes used to illustrate the current invention are available commercially. Details of the purifications from natural sources are shown in table 5. Purification from a recombinant source can be achieved by one of several standard methods including the use of a histidine tag as an extension to the protein for purification on a nickel chelating affinity column (used for purification of TEV protease).

TABLE 5

| Protease | Source | Reference |
| --- | --- | --- |
| Chymotrypsin | bovine pancreas | |
| Thrombin | bovine plasma | |
| TEV | recombinant, *E.coli* (histidine tag) | Life Technologies Ltd. |
| Aminopeptidase M | porcine kidney | |
| Carboxypeptidase P | *Penicillium janthinellum* | |

TABLE 5-continued

| Protease | Source | Reference |
|---|---|---|
| Carboxypeptidase Y | yeast | Hayashi et al., (1973) J. of Biol. Chem. 248:2296. |

Design of Binding Domains and Modification Sites

Placement of a modification site on a binding partner polypeptide may be determined empirically, such that the location itself permits the interaction between the binding domain, sequence, or polypeptide and a binding partner, but such that the association is altered on modification of the site. This change in association may be a direct or indirect consequence of modification. While not being bound to any theory, such a change may be based on, for example, a conformational or electrostatic change brought about by phosphorylation or dephosphorylation. In cases where there is no appropriate structural information, the modification sites will also be determined empirically.

According to the invention, a natural or engineered binding domain is selected such that its association with a binding partner is dependent upon modification at a site for modification which naturally occurs within, is introduced into- or altered within- a binding domain of one or both of the binding partner polypeptides. Any engineering of the modification site or binding domain is performed by molecular methods which are well known in the art, as described below.

The location of the modification site must be such that it is tolerated in one state of modification (for example, prior to modification), but provokes dissociation of the complex in the opposite state of modification (following modification; or vice versa). As stated above, placement of the modification site within the domain may involve empirical testing on a case-by-case basis; however, such testing can be facilitated through the use of knowledge of the structural basis of the interaction sites in the complex. Such knowledge may be structural (e.g., using crystallographic data or a molecular modeling algorithm of the 3-dimensional structure of the protein or proteins involved in the complex of interest), a functional assessment of the regions of primary sequence important in binding, or a combination of these. These data will identify regions of the protein most likely to be influenced by the insertion of a modification site.

The contact face between components of the complex is one location at which a site for modification might occur naturally or be engineered, but it is not the only useful location. The modification of a site remote from the interface site(s) can also lead to binding or dissociation of the complex. This would be expected to occur upon long-range alterations in protein structure as a consequence of the post-translational modification, which could be as extreme, for example, as structural collapse following modification.

For example, a peptide, PKI(5–24amide), derived from a protein inhibitor of the cAMP-dependent protein kinase binds to the active site of protein kinase A (PKA) with high affinity. The 3-D structure of this complex is known (Knighton et al., (1991) *Science*, 253:414) as is a functional dissection of the sequence of this peptide to identify residues involved in this biological activity (Glass et al., (1989) *J. Biol. Chem.*, 264:8802). The binding of PKI(5–24amide) to the catalytic subunit of PKA can be monitored by a number of techniques including FRET, fluorescence correlation spectroscopy (FCS), or fluorescence anisotropy provided both components in the former case or the PKI(5–24amide) component in the latter two cases, respectively, are labeled with appropriate fluorophores.

The introduction of a PKA phosphorylation site into this peptide, by mutation of Ala$^{21}$Ser (called PKI(A21S) hereinafter), can result in a reporter molecule for protein kinase A activity. In an assay of the invention, PKI(A21S) can bind to PKA when dephosphorylated, but will dissociate from the enzyme once phosphorylated.

Molecular Methods Useful in Producing a Binding Domain

A natural or engineered binding domain of use in the invention can be produced using molecular methods such as are known in the art (see, for example, Sambrook et al., 1989; Ausubel et al.). Such methods include chemical synthesis of a polypeptide sequence that encompasses a natural or engineered binding domain or expression of a recombinant polynucleotide encoding such a molecule. Such a polynucleotide may be chemically synthesized; however, of particular use in the invention are methods of in vitro or otherwise site-directed mutagenesis by which to engineer a site for post-translational modification into an existing binding domain (whether natural or previously engineered) or by which to alter the enzyme specificity of an existing site.

Typically, methods for in vitro mutagenesis comprise the annealing of a mutagenic oligonucleotide primer comprising the desired alteration to a complementary, single-stranded template, followed by second strand synthesis, whether using single-cycle synthesis or polymerase chain reaction (PCR). Cloning and sequencing are then performed to identify and isolate molecules bearing the desired alterations. Such mutagenesis methods optionally include a selection for mutated molecules, either through the use of modified nucleotides incorporated into the nascent polynucleotide strand or through the incorporation of a restriction site into the vector bearing the first strand which is disrupted in the second strand (i.e., in coupled priming; Carter et al., (1985) *Nucleic Acids Res.*, 13:4431) and, with either technique, subsequent transformation of the first and second strands into a strain of host cells that selectively destroys the first strand and propagates the second.

Kits and individual components for in vitro mutagenesis enjoy wide commercial availability. A non-limiting sampling of such kits is as follows:

From Stratagene (LaJolla, Calif., U.S.A.): ExSite™ PCR-Based Site-Directed Mutagenesis Kit (catalog number: 200502); QuikChange™ Site-Directed Mutagenesis Kit (catalog number: 200518); and Chameleon™ Double-Stranded, Site-Directed Mutagenesis Kit (catalog numbers: 200508 and 200509).

From Promega (Madison, Wis., U.S.A.): Interchange™ in vivo Amber Suppressor Mutagenesis System (catalog number: Q5080); Altered Sites® II in vitro Mutagenesis Systems (catalog numbers: Q6210, Q6090 and Q6080); GeneEditor™ in vitro Site-Directed Mutagenesis System (catalog number: Q9280); and Erase-a-Base® System (catalog numbers E5850 and E5750).

From New England Biolabs (Beverly, Mass., U.S.A.): Code20™ Cassette Mutagenesis System (catalog number: 7520). All such kits are used according to the manufacturer's instructions.

Non-limiting examples of pairs of amino acid sequences which associate in nature and can be engineered to provide engineered binding domains, sequences or polypeptides of use in the invention are presented in Table 6.

TABLE 6

| Class | Subclass | Partner 1 | Possible positions for engineered sites | Partner 2 | Possible positions for engineered sites |
|---|---|---|---|---|---|
| INTRA-MOLECULAR | | PKC pseudo-RACK site♣ Hemolin domains 1, 2 M63398 | | PKC RACK binding site♣ Hemolin domains 3, 4 M63398 | |
| HOMO-OLIGOMER | | PKA RIIβ M31158 | 1–36 | PKA RIIβ M31158 | 1–36 |
| | | MetJ monomer M12869 | 20–29, 52–66 | MetJ monomer M12869 | 20–29, 52–66 |
| | | Phospholamban M60411 | 18–31 | Phospholamban M60411 | 18–31 |
| HETERO-OLIGOMER | SH2♠ | Src K03218 | 150–247 | RACK1 M24194 | |
| | | RasGAP M23379 (human) | 181–272, 351–441 | EphB2 L25890 (mouse) AF025304 (human) | juxta-membrane region, including 604–613 (mouse) |
| | SH3 | ArgBP2 AF049884 | 436–484, 614–664 | Arg** | pro rich region 2 |
| | | CRKL X59656 | 123–296 | Abl 1 X16416 | 782–1019 |
| | PDZ | nNOS U17327 | 1–195 | PSD 95 U83192 | 138–294 |
| | | PTP-BL Z32740 | 1352–1450, 1756–1855 | RIL Y08361 | 249–330 (LIM domain) |
| | PH | IRS 1 S62539 | 157–267 | IL4-R X52425 | 489–499 |
| | | cbl X57110 | 1–357 | ZAP 70 L05148 | 284–299 |
| | WW | Nedd4 D42055 | 218–251, 375–408, 448–481, 500–533 | Amiloride-sensitive Na⁺ channel β subunit L36593 γ subunit L36592 | C-terminal P2 region |
| | AKAP | AKAP 79 M90359 | 388–409 | PKA RIIβ M31158 | 1–36 |
| | | AKAP 79 M90359 | 31–52 | PKC α, β1, β2∞ | |
| | | ADAP 79 M90359 | 81–102 | Calcineurin (A subunit) M81483 | |
| | | Gravin U81607 | 1537–1563 | PKA RIIβ M31158 | 1–45 |
| | | Gravin U81607 | 265–556 | PKC β2⊗ | |
| | RACK | RACK1 M24194 | | PKCβ1 X06318, M27545 | 186–198, 209–226 |
| | | β'COP X70476 | | PKCε X65293, S46030 | 2–145 |
| | YXDED | ZIP♦ Y08355 | 41–105 | PKC ζ♦ | 79–145 |

♣Ron and Mochly-Rosen, (1995) *Proc. Natl. Acad. Sci. U.S.A.*, 92:492. The association of these two regions will have a number of determinants other than the engineered chemical modification in vivo including the presence or absence of PKC activators (such as phosphatidylserine, $Ca^{2+}$ and diacylglycerol) or endogenous RACK1. This might complicate interpretation of the assay in vivo, however it should provide a useful module on which to build an in vitro assay.

♠In order for the SH2 domain to be useful in an assay of this type it must be modified such that the addition or removal of a phosphate group from a tyrosine residue is no longer a determinant of binding. This could be achieved by thiophosphorylation of the Tyr residue in an in vitro assay to yield a permanently phosphorylated protein. Alternatively, it may be possible to mimic phosphorylation by the mutation of the key Tyr residue to Glu or Asp. If this were possible then these domains could be used in an in vivo assay.

** Wang et al., 1997, *J. Biol. Chem.*, 272:17542–17550.

∞ Konishi et al., 1994, *Biochem. Biophys. Res. Comm.*, 205:1770–1775.

Ⓧ Nauert et al., 1997, *Curr. Biol.* 7:52–62.
♦ Puls et al., 1997, *Proc. Natl. Acad. Sci. U.S.A.*, 94:6191–6196.

ZIP contains more than one protein binding motif (YXDED motif, ZZ zinc finger) and is known to bind to several proteins other than PDCζ (including p62 and EBIAP) and also to self-associate (this self association is in competition with PKCζ binding). These multiple interactions may cause problems with an in vivo assay as it is not clear whether any of the proteins bind in a competitive manner.

Selection of Functional Partners Sensitive to Post-Translation Modification

A natural or engineered binding domain can be assayed for modification-dependent binding to a binding partner, for example to a binding partner to which it was known to associate with naturally or prior to engineering. If binding of the binding domain and the binding partner is determined to be modification-sensitive (i.e., such that the binding domain and the binding partner either do- or do not associate, depending upon modification of the modification site), the binding domain and binding partner (or "pair of binding partners") are useful in assays of enzymatic activity according to the invention.

Alternatively, candidate binding partners can be screened for their ability to bind the binding domain in a modification-dependent manner. Such binding partners may be selected or designed based upon sequence homology with known binding partners or on molecular modeling data (e.g., from a modeling algorithm). Potential binding partners additionally can be purified (e.g., using the binding domain as the trap in affinity chromatography or as a probe for a library) from a population of polypeptide molecules. A library from which to draw a diverse population of polypeptide sequences of use in the invention includes, but is not limited to, an expression library or a synthetic peptide library.

One library-based technique which is useful in the invention to generate new pairs of assay components is that of phage display, which provides convenient testing of polypeptide sequences able to complex with the target sequence from a vast repertoire of different polypeptide sequences.

Filamentous bacteriophage display a small number of copies of a protein termed g3p on their surface. This protein is responsible for interacting with proteins on the surface of *Escherichia coli* and facilitates the infection of the bacterium. This protein possesses three globular domains linked by protease resistant, flexible amino acid sequences. The g3p protein can be modified to provide a means of presenting protein structures from which proteins capable of forming a stable binding complex can be identified. Such a bioassay can be configured in a number of ways including:

a) Expression of the test proteins as an extension of the g3p sequence. Proteins able to bind with target polypeptide A can be selected by affinity purification on a matrix displaying polypeptide A.

b) Expression of the test protein as an extension of the g3p protein, plus independent expression from the same phage of the target protein (polypeptide A) fused to a convenient affinity tag (such as His$_6$). The binding of polypeptide A to the test protein displayed on g3p will facilitate the affinity purification of this phage particle.

c) Expression of the test protein and polypeptide A as an interruption of the g3p sequence, preferably at one of the linker regions. This can produce fusion proteins of g3p$_{N\text{-}term}$:polypeptide A and test protein partner B:g3p$_{C\text{-}term}$, to which phage infective properties are only restored if polypeptide A and the test partner B bind to each other with reasonable affinity. This technique has been adapted from those previously described (Spada and Pluckthun, (1997) *Nature Medicine*, 3:694; Sieber et al., (1998) *Nature Biotechnology*, 16:955; Kristensen and Winter, (1990) *Folding and Design*, 3:321).

If A has a site for post-translational modification, then binding partners tolerant of that site can be identified. A second round of selection can then be undertaken to identify the binding partners which dissociate upon post-translational modification of that site (i.e., those to which binding of the binding domain is dependent upon post-translational modification).

The complex between an engineered or natural binding domain and a binding partner may comprise a self-associated polypeptide monomer or, alternatively, either a hetero-oligomer or a homo-oligomer.

Tags

A binding partner polypeptide can further comprise a tag or tags (label or labels). Only one of the binding partners can comprise a tag or tags. Optionally, both binding partner polypeptides can comprise a tag or tags. More than one enzyme can be assayed a time where different tags are placed on different pairs of binding partner polypeptides. Preferably, different tags are positioned on at least 1, 2, 3, 4, 5, 10, or more binding partner polypeptide pairs and at least 1, 2, 3, 4, 5, 10, or more enzymes are assayed simultaneously.

A tag allows for the interaction of a tagged binding partner polypeptide with a detection molecule or with another tag, such that the tag can be detected. Optionally, the tag can be directly detected.

A tag can comprise, but is not limited to an antigen or an epitope tag such as myc (Roth et al., (1991) *J. Cell Biol.* 115:587; HA, derived from influenza hemagglutining protein (Wilson et al., (1984) *Cell* 37:767; FLAG (U.S. Pat. Nos. 4,793,004; 4,851,341); IRS (RYIRS (SEQ ID NO:53) or IRS antibodies available from Berkeley Antibody Company, Richmond Calif., (BAbCO)); AU1 (DTYRYI (SEQ ID NO:54), antibodies available from BAbCO); AU5 (TDFLYK (SEQ ID NO:55), antibodies available from BAbCO); glu-glu (EEEEYMPME (SEQ ID NO:56), antibodies available from BAbCO); KT3 (KPPTPPPEPET (SEQ ID NO:57), antibodies available from BAbCO); T7 Tag™ (antibodies available from Novagen, Madison, Wis.); HSV Tag™ (antibodies available from Novagen); and S-Tag™ (antibodies available from Novagen), VSV-G (antibodies available from Research Diagnostics, Inc., Flanders N.J.), and His Tag (antibodies available from Research Diagnostics, Inc., Flanders N.J.). A tag can further comprise an antibody, a single-chain antibody, a coiled-coil region, sequence specific nucleic acid binding domains, such as DNA or RNA binding domains, SH3 or SH2 peptide interactions, metal chelating amino acids (Porath et al., (1975) *Nature* 258:598; Lonnerdal et al., (1982) *J. Appl. Biochem.* 4:203; Sulkowski, (1985) *Trends Biotechnol.* 3:1; U.S. Pat. No. 5,047,513), a fluorochrome, a fluorescent protein, including green-fluorescent proteins, blue-fluorescent proteins, and red-fluorescent proteins, a molecule that quenches a fluorescent molecule, a radioactive amino acid or amino acids, a radioisotope, a radionuclide containing molecule, a reporter enzyme, such as luciferase (Brasier et al., (1989) *Bio Techniques* 7:1116), chloramphenicol acetyltransferase (CAT) (Gorman et al., (1982) *Mol. Cell Biol.* 2:1044), horseradish peroxidase, alkaline phosphatase, glucose oxidase, hexokinase with glucose-6-phosphate dehydrogenase, or β-galactosidase (An et al., (1982) *Mol. Cell Biol.* 2:1628), or a biotin molecule and analogs and derivatives thereof. Antigens such as, but not limited to, glutathione S-transferase (GST), green-fluorescent protein (GFP) from *Aequorea Victoria*, β-glucuronidase, β-galactosidase, and biotin can be used as binding partner tags. Any antigen or epitope for which a substantially pure antibody can be isolated or produced can be used as a tag according to the present invention.

A binding partner polypeptide can be produced and a recombinant, synthetic, or naturally purified tag subsequently added by covalent or non-covalent attachment or a binding partner polypeptide can be produced with a tag, i.e., a fusion protein. A tag can be non-covalently or covalently attached to a recombinantly produced or synthesized binding partner polypeptide. For example, a tag comprising biotin, its derivatives, or its analogs can be covalently attached to a binding partner polypeptide using a biotinylation reagent. Biotinylation reagents target a variety of functional groups, including, but not limited to primary amines, sulfhydryls, carboxyls, carbohydrates, tyrosine, and histidine side chains. Other tags such as antigens and coiled-coils can also be attached to a binding partner by covalently linking the two protein segments using techniques well known in the art. Optionally, a binding partner polypeptide can be produced with a tag such as in a fusion protein or by total chemical synthesis of proteins (Gryphon Sciences, South San Francisco Calif.).

A coiled-coil domain can be used as a tag for an isolated binding partner polypeptide. The use of a tag such as a coiled-coiled allows for a specific and controllable method of labeling binding partner polypeptide domains at predictable locations. A coiled-coil domain is structurally conserved among many proteins that interact to form homo- or heterodimeric oligomers. A leucine zipper motif provides an example of a coiled-coil protein structural motif. Examples of pairs of leucine zipper containing proteins include the fos gene product and the jun gene product. A leucine zipper motif is found in, among other examples, a nuclear protein that functions as a transcriptional activator of a family of genes involved in the General Control of Nitrogen (GCN4) metabolism in *S. cerevisiae*. The protein is able to dimerize and bind promoter sequences containing the recognition sequence for GCN4, thereby activating transcription in times of nitrogen deprivation.

Coiled-coils are α-helical oligomers or bundles with between 1 and 5 polypeptide strands with the following characteristics: a sequence hallmark of a predominance of hydrophobic residues (in particular alanine, isoleucine, leucine, methionine or valine) spaced 3 and 4 residues apart in the primary sequence which is repeated three or more times in near or exact succession (canonical heptad coiled-coil repeat, abbreviated to $(3,4)_n$ where n=3 or greater). The hydrophobic residues are present at the 'a' and 'd' positions within a heptad when the amino acids are identified as positions a, b, c, d, e, f, and g by order of sequence. In addition, spacing of hydrophobic residues in patterns of 3, 4, 4 and 3, 4, 3 (hendecad repeat) have been reported (Hicks et al., (1997) *Folding and Design*, 2:149) and are compatible with the coiled-coil structure. Additionally, in structural terms coiled-coil helical bundles have between 2 and 5 helices which are offset at roughly 20° to adjacent strands with the hydrophobic side chains interdigitating in the interface between helices in what is termed the "knobs into holes" packing (Crick, (1953) *Acta. Crystallogr.*, (6:689).

Natural and non-natural coiled-coils can have parallel and/or antiparallel helices. Both homotypic (multiple strands of identical sequence) and heterotypic bundles have been described.

Leucine zipper sequences conform to the coiled-coil rules above and typically have leucine residues at the 'd' position of the canonical heptad repeat. These leucine residues represent a single face of the helix. Interdigitating with these leucine residues are valine residues. The combination of these residues forms a continuous hydrophobic face which associates with an equivalent region in an associating subunit. Alternatively, the hydrophobic face can be discontinuous due to interruptions in the heptad repeat sequence. This, however, does not interfere with the ability of these coiled-coils to interact. The stability of the dimer thus formed is conferred by the hydrophobic interactions between the leucine and valine residues and hydrogen bonds that form between residues present on the two interacting helices. Interestingly, the coiled-coil domain of GCN4 has been shown to dimerize as an isolated peptide (Gonzalez et al., (1996) *Nature Structural Biology*, 3:1011).

Examples of naturally-occurring coiled-coils are found in the following references: Stone & Smillie, (1978) *J. Biol. Chem.* 253:1137; Blake et al., (1995), *Trends Biochem. Sci.*, 20:133; Hinnebusch, (1984) *Proc. Natl. Acad. Sci. U.S.A.*, 81:6442; van Straaten et al., (1983) *Proc. Natl. Acad. Sci. U.S.A.*, 80:3183; Hattorie et al., (1988), *Proc. Natl. Acad. Sci. U.S.A.*, 85:9148; Hartlein et al., (1987) *Nucleic Acids Res.*, 15:1005; Biou et al., (1994), *Science*, 263:1404; Stebbins et al., (1995) *Nature*, 373:636; Harbury et al., (1994) *Nature*, 371:80; Lovejoy et al., (1993) *Science*, 259:1288; Casareni et al., (1982) *Proc. Natl. Acad. Sci. U.S.A.*, 79:6313; and Simmerman et al., (1996) *J. Biol. Chem.* 271:5941.

Both heterodimeric and homodimeric coiled-coil polypeptides can be used as tags for isolated binding partner polypeptides. A first part of a heterodimer or homodimer coiled-coil polypeptide (the tag) is attached to a binding partner as, for example, a fusion protein, or by covalent or non-covalent attachment. Thus, the first part of the heterodimer or homodimer can be specifically and predictably placed in a binding partner polypeptide. A second part of the heterodimer or homodimer coiled-coil polypeptide (the detector molecule) can be, for example, chemically synthesised or produced recombinantly and labeled with one or more reporter molecules, for example, an antigen, an antibody, a single chain antibody, biotin, radioactive amino acids, a reporter enzyme, a chemical fluorophore, or a fluorescent protein. Optionally, the second part of the heterodimer or homodimer can be produced as a fusion protein with a reporter molecule. The first part of the heterodimer or homodimer carrying the unlabeled coil partner attached to the binding partner is mixed with the tagged second part of the homodimer or heterodimer in conditions allowing coiled-coil formation. The formation of a coiled-coil dimer will stably attach the tag to the binding partner polypeptide. The mixing can occur prior to the use of the tagged binding partner in an assay or it can occur during the assay, i.e., by mixing all components of an assay at once. Use of heterodimeric coiled-coil peptides enables specific labeling of different protein domains, because specific heterodimers will not cross react with each other. This will also enable FRET based assays or multiple enzyme FP assays to be performed.

The use of a tag, such as a coiled-coiled, allows for a specific and controllable method of labeling binding partner polypeptide domains at predictable locations. The ability to provide a tag at a predictable location on a binding partner polypeptide is very advantageous. For example, a chemical fluorophore can be coupled to various positions on a coiled-coil heterodimer or homodimer for optimal effect in subsequent fluorescent assays. The length of a linker between the coil and a binding partner polypeptide can also be varied to position the fluorescent molecule at different distances from the protein and also to allow more or less flexibility and movement between the binding partner and the fluorescent molecule.

Detection and Detector Molecules

A tagged polypeptide of the invention can be directly or indirectly detected. Examples of directly detectable tags include fluorescent molecules and fluorescent proteins and radioisotopes. For indirect detection a tag is bound by a detection molecule which incorporates a detectable moiety (or a reporter region).

A detector molecule comprises a first region that associates with a tagged isolated binding partner and a second region comprising a reporter region. The first region can associate covalently or non-covalently with the tagged binding partner. For example, the first region can be an antibody that binds to an antigen or epitope tag or an antigen or epitope that binds to an antibody tag as disclosed in "Tags" section above. Examples include FLAG/anti-FLAG antibody (Chiang et al., (1993) *Peptide Res.* 6:62; Brizzard et al., (1994) *Biotechniques.* 16:730); Fc region immunoglobulin/protein A (Uhlen et al. (1983) *Gene* 23:369), c-myc/Mab (Kolodziej et al., (1991) *Meth. Enzymol.* 194:508; Evan et al. (1985) *Mol. Cell. Biol.* 5:3610); HA epitope/antibody (See e.g., Howard et al. (1995) *Am J. Physiol.* 269:C1565; Xie, (1998) *Endocrinology* 139:4563); vsv-G, mT/antibody or His tag/anti-His antibody (Ford et al., (1991) *Protein Expr. Purif.* 2:95). See also Nilsson et al., (1996) *J. Mol. Recognit.* 9:585. Further, the first region of the detector molecule can be an avidin or streptavidin molecule that binds to a biotin tag on a polypeptide, or one part of a homodimer or heterodimer coiled-coil that associates with a second part of a homodimer or heterodimer coiled-coil on a binding partner. The first region of the detector molecule can also be an oligonucleotide, comprising DNA or RNA, that binds to a corresponding nucleic acid binding domain or binding partner.

The detector molecule further comprises a second region comprising a reporter region. A reporter is a molecule which can be conjugated or otherwise attached (i.e., covalently or non-covalently) to a the first region of the detector molecule. A reporter region can comprise more than one reporter molecule, such as at least 2, 3, 4, 5, or 10 reporter molecules. For example a reporter region can comprise two or more fluorochromes or two or more radioisotopes for signal enhancement. Reporters include fluorochromes such as phycoerythin (PE.), phycoerythrin-cyanin dye 5 (PECy5), rhodamine, and fluorescein isothiocyanate (FITC). Fluorescent protein tags, such as green fluorescent proteins, blue fluorescent proteins, red fluorescent proteins and variants thereof can be used. Other suitable detectable reporters include those useful in colorimetric enzyme systems, e.g., horseradish peroxidase (HRP), alkaline phosphatase (AP), hexokinase in conjunction with glucose-6-phosphate dehydrogenase, β-galactosidase, and glucose oxidase. Radioactive compounds or elements, such as radioactive amino acids, radioisotopes, or radionuclide containing molecules can also be used as reporters. The reporter molecules used may be readily selected by one of skill in the art and are not a limitation on the present invention.

Optionally, a detector molecule is mixed with a tagged binding partner polypeptide prior to use of the tagged binding partner in an assay or kit of the invention. Thus, a tagged binding partner can be provided with a pre-bound detector molecule or without a pre-bound detector molecule.

Detector molecules are commercially available. Additionally, detector molecules can be produced using molecular methods known in the art. Preferably, the two regions of a detector molecule are produced as a fusion protein. A detector molecule can also be chemically synthesized.

Immobilization of a Binding Partner Polypeptide

A binding partner polypeptide comprising a binding domain can optionally be attached or immobilized to any type of solid support known in the art, while its binding partner polypeptide is not immobilized. Alternatively, both binding partners can be immobilized or both binding partners can be free. For example, an immobilized polypeptide can be attached to microtiter plate (e.g. PVC or polystyrene), a membrane such as nitrocellulose, or a disc or bead comprising for example, glass, fiberglass, latex, magnetic material, or agarose. The support can also comprise a magnetic particle or a fiber optic sensor.

A polypeptide of the invention can be attached or immobilized to the solid support by any of the methods known in the art. For example, a polypeptide can be attached to a solid support by noncovalent or covalent attachment. Covalent attachment can be accomplished by a direct linkage between the polypeptide and functional groups on the support or by a cross-linking agent. For example, covalent attachment can be achieved by reacting the support with a bifunctional reagent that will react with both the support and a functional group, such as a hydroxyl or amino group on the polypeptide.

Further, a polypeptide can be biotinylated and covalently attached to a microtiter plate that has been pre-coated with, for example, streptavidin. A polypeptide can also be produced with a His tag (i.e. approximately 6 His residues) such that the polypeptide binds to a microtitre plate coated with nickel chelate. Where a polypeptide of the invention is immobilized on a solid support, only one of the binding partners, preferably the free binding partner polypeptide, is required to be tagged; however, both binding partners can be tagged.

Optionally, at least 1, 2, 3, 4, 5, 10, 50, 100, 1,000, 10,000, or more different binding partner polypeptides are immobilized on a solid support such that each binding partner polypeptide is immobilized in a known location. See e.g. U.S. Pat. No. 5,744,305. Because each type of binding partner is spatially separated and occurs at a specific location, the effect of numerous enzymes on many binding partners can be assayed at once. Preferably, 1, 2, 3, 4, 5, 10, 20, 100, 1,000 or more enzymes are assayed simultaneously.

Methods of Monitoring the Activity of One or More Enzymes

According to the invention, the activity of modifying enzyme or enzymes are assayed by measuring the formation or destruction of protein:protein complexes when the modifying enzyme is present with binding partner polypeptides comprising one or more sites for modification, under conditions which permit modifying activity. Methods which enable the detection of protein:protein complexes (i.e., methods which allow one of skill in the art to discriminate between polypeptide pairing partners which are bound and those which are unbound) are known in the art. Of particular use in the invention are those methods which entail fluorescent labeling of the binding partner polypeptides, and subsequent detection of changes in fluorescence, whether in frequency or level, following incubation of the labeled assay components with the candidate modifying enzyme. Several such procedures are briefly summarized below.

Fluorescent Resonance Energy Transfer (FRET)

A tool with which to assess the distance between one molecule and another (whether protein or nucleic acid) or between two positions on the same molecule is provided by the technique of fluorescent resonance energy transfer (FRET), which is now widely known in the art (for a review, see Matyus, (1992) *J. Photochem. Photobiol. B: Biol.,* 12:323). FRET is a radiationless process in which energy is transferred from an excited donor molecule to an acceptor molecule; the efficiency of this transfer is dependent upon the distance between the donor and acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favorable pairs of donor and acceptor.

Radiationless energy transfer is based on the biophysical properties of fluorophores. These principles are reviewed elsewhere (Lakowicz, 1983, *Principles of Fluorescence Spectroscopy,* Plenum Press, New York; Jovin and Jovin, 1989, *Cell Structure and Function by Microspectrofluorometry,* eds. E. Kohen and J. G. Hirschberg, Academic Press). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labeled for use either in vivo or in vitro by methods known in the art. According to the invention, binding partner polypeptides, comprising either the same or different polypeptide molecules, are differentially labeled, one with a donor and the other with an acceptor, and differences in fluorescence between a test assay, comprising a protein modifying enzyme, and a control in which the modifying enzyme is absent, are measured using a fluorimeter or laser-scanning microscope. Preferably, one binding partner is immobilized on a solid support. It will be apparent to those skilled in the art that excitation/detection means can be augmented by the incorporation of photomultiplier means to enhance detection sensitivity. The differential labels may comprise either two different fluorescent labels (e.g., fluorescent proteins as described below or the fluorophores rhodamine, fluorescein, SPQ, and others as are known in the art) or a fluorescent label and a molecule known to quench its signal; differences in the proximity of the binding domain to its binding partner with- and without the protein-modifying enzyme can be gauged based upon a difference in the fluorescence spectrum or intensity observed.

This combination of protein-labeling methods and devices provides measurements of the activity of the protein modifying enzyme in real time (i.e., as a reaction progresses). This allows both rapid data collection and yields information regarding reaction kinetics under various conditions.

A sample, whether in vitro or in vivo, assayed according to the invention therefore comprises a mixture at equilibrium of the labeled binding domain and its binding partner which, when disassociated from one another, fluoresce at one frequency and, when complexed together, fluoresce at another frequency or, alternatively, of molecules which either do or do not fluoresce depending upon whether or not they are associated.

A fluorescent label is either attached to the surface of the binding partner polypeptides or, alternatively, a fluorescent protein is fused in-frame with a binding partner polypeptide, as described below. The choice of fluorescent label will be such that upon excitation with light, labeled peptides which are associated will show optimal energy transfer between fluorophores. In the presence of a protein modifying enzyme (e.g., a phosphorylating-, a dephosphorylating-, a ubiquitinating-, ADP-ribosylating-, sentrinizing, prenylating- glycosylating- or proteolyzing enzyme), a complex comprising binding partners dissociates due to structural or electrostatic disruption which occurs as a consequence of modification of the enzyme recognition site, thereby leading to a decrease in energy transfer and increased emission of light by the donor fluorophore. Alternatively, the binding partner polypeptides can associate in the presence of a protein modifying enzyme. In this way, the state of polypeptide modification can be monitored and quantitated in real-time.

As used herein, the terns "fluorescent molecule" and "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 7.

TABLE 7

| Fluorophore | Excitation (nm) | Emission (nm) | Color |
| --- | --- | --- | --- |
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |

TABLE 7-continued

| Fluorophore | Excitation (nm) | Emission (nm) | Color |
|---|---|---|---|
| Rhodamine (TRITC) | 552 | 570 | red |
| Quantum Red ™ | 488 | 670 | red |
| PKH26 | 551 | 567 | red |
| Texas Red | 596 | 620 | red |
| Cy3 | 552 | 570 | red |

Examples of fluorescent proteins which vary among themselves in excitation and emission maxima are listed in Table 1 of WO 97/28261 (Tsien et al., 1997). These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/408], S65T [489/511], P4-1 [504(396)/480], S65A [471/504], S65C [479/507], S65L [484/510], Y66F [360/442], Y66W [458/480], I0c [513/527], W1B [432(453)/476(503)], Emerald [487/508] and Sapphire [395/511]. Red fluorescent proteins such as DsRed (Clontech) having an excitation maximum of 558 nm and an emission maximum of 583 can also be used. This list is not exhaustive of fluorescent proteins known in the art; additional examples are found in the Genbank and SwissProt public databases.

A number of parameters of fluorescence output are envisaged including 1) measuring fluorescence emitted at the emission wavelength of the acceptor (A) and donor (D) and determining the extent of energy transfer by the ratio of their emission amplitudes;

2) measuring the fluorescence lifetime of D;

3) measuring the rate of photobleaching of D;

4) measuring the anisotropy of D and/or A; or 5) measuring the Stokes shift monomer; excimer fluorescence.

Certain of These Techniques are Presented Below.

Fluorescent Labels

In a FRET assay of the invention, fluorescent labels (tags) are chosen such that the excitation spectrum of one of the labels (the acceptor label) overlaps with the emission spectrum of the excited fluorescent label (the donor label). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by binding partner polypeptides labeled with different fluorescent labels, wherein one is linked to a donor and the other to an acceptor label, in monitoring protein modification according to the present invention. A single polypeptide may comprise a blue fluorescent protein donor label and a green fluorescent protein acceptor label, wherein each is fused to a different assay component (i.e., in which one is fused to a binding partner polypeptide); such a construct is herein referred to as a "tandem" fusion protein. Alternatively, two distinct polypeptides ("single" fusion proteins) one comprising a binding partner polypeptide and the other its binding partner may be differentially labeled with the donor and acceptor fluorescent protein labels, respectively. The construction and use of tandem fusion proteins in the invention can reduce significantly the molar concentration of peptides necessary to effect an association between differentially-labeled polypeptide assay components relative to that required when single fusion proteins are instead used. It is essential that sufficient distance be placed between the donor and acceptor by the linker and/or the binding domain and its binding partner to ensure that FRET does not occur unless the binding domain and its binding partner bind. The labeled binding partner polypeptides may be produced via the expression of recombinant nucleic acid molecules comprising an in-frame fusion of sequences encoding such a polypeptide and a fluorescent protein label either in vitro (e.g., using a cell-free transcription/translation system, or instead using cultured cells transformed or transfected using methods well known in the art) or in vivo, for example in a transgenic animal including, but not limited to, insects, amphibians, and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a linker, a secretion signal, a nuclear localization signal or other primary sequence signal capable of targeting the construct to a particular cellular location, if it is so desired.

The means by which binding partners are assayed for association using fluorescent labels according to the invention may be briefly summarized as follows:

Whether or not the binding partner polypeptides are present on a single polypeptide molecule, one is labeled with a green fluorescent protein, while the other is preferably labeled with a red or, alternatively, a blue fluorescent protein. Useful donor:acceptor pairs of fluorescent proteins (see Tsien et al., 1997, WO 97/28261) include, but are not limited to:

Donor: S72A, K79R, Y145F, M153A and T203I (excitation λ 395 nm; emission λ 511)

Acceptor: S65G, S72A, K79R and T203Y (excitation λ 514 nm; emission λ 527 mn); or T203Y/S65G, V68L, Q69K or S72A (excitation λ 515 mn; emission λ 527 nm).

An example of a blue:green pairing is P4-3 (shown in Table 1 of Tsien et al., 1997) as the donor label and S65C (also of Table 1 of Tsien et al., 1997, supra) as the acceptor label. The binding partner polypeptides are exposed to light at, for example, 368 nm, a wavelength that is near the excitation maximum of P4-3. This wavelength excites S65C only minimally. Upon excitation, some portion of the energy absorbed by the blue fluorescent protein label is transferred to the acceptor label through FRET if the binding partners are in close association. As a result of this quenching, the blue fluorescent light emitted by the blue fluorescent protein is less bright than would be expected if the blue fluorescent protein existed in isolation. The acceptor label (S65C) may re-emit the energy at longer wavelength, in this case, green fluorescent light.

After modification of one or both of the binding partners by a protein modifying enzyme, the binding partners (and, hence, the green and red or, less preferably, green and blue fluorescent proteins) physically separate or associate, accordingly inhibiting or promoting FRET. For example, if activity of the modifying enzyme results in dissociation of a protein:protein complex, the intensity of visible blue fluorescent light emitted by the blue fluorescent protein increases, while the intensity of visible green light emitted by the green fluorescent protein as a result of FRET, decreases.

Such a system is useful to monitor the activity of enzymes that modify one or more binding partners to which the fluorescent labels are fused as well as the activity of protein modifying enzymes or candidate modulators thereof.

In particular, this invention contemplates assays in which the amount- or activity of a modifying enzyme in a sample is determined by contacting the sample with binding partner polypeptides, differentially-labeled with fluorescent proteins, as described above, and measuring changes in fluorescence of the donor label, the acceptor label or the relative fluorescence of both. Fusion proteins, as described above, which comprise either one or both of the labeled binding partner polypeptides in an assay of the invention can be used for, among other things, monitoring the activity of a protein modifying enzyme inside the cell that expresses the recombinant tandem construct or two different recombinant constructs.

Advantages of single- and tandem fluorescent protein/polypeptides comprising a binding partner polypeptide fused to a fluorescent protein include the greater extinction coefficient and quantum yield of many of these proteins compared with those of the Edans fluorophore. The acceptor in such a construct or pair of constructs is, itself, a fluorophore rather than a non-fluorescent quencher like Dabcyl. Alternatively, in single-label assays of the invention, whether involving use of a chemical fluorophore or a single fluorescent fusion construct, such a non-fluorescent quencher may be used. Thus, the enzyme's substrate (i.e., the binding domain of a binding partner polypeptide and, optionally, the corresponding binding partner), and reaction products (i.e., the binding domain of a binding partner polypeptide and, optionally, the corresponding binding partner after modification) are both fluorescent but with different fluorescent characteristics.

In particular, the substrate and modified products exhibit different ratios between the amount of light emitted by the donor and acceptor labels. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, *Aequorea*-derived or -related fluorescent protein labels tend to be protease resistant. Therefore, they are likely to retain their fluorescent properties throughout the course of an experiment.

Alternative Fluorescent Techniques Suitable for Monitoring Protein: Protein Binding One embodiment of the technology can utilize monomer:excimer fluorescence as the output.

The fluorophore pyrene when present as a single copy displays fluorescent emission of a particular wavelength significantly shorter than when two copies of pyrene form a planar dimer (excimer). As above, excitation at a single wavelength (probably 340 nm) is used to review the excimer fluorescence (~470 nm) over monomer fluorescence (~375 nm) to quantify assembly:disassembly of the binding partner polypeptides.

Further embodiments of the present invention are not dependent on FRET. For example the invention can make use of fluorescence correlation spectroscopy (FCS), which relies on the measurement of the rate of diffusion of a label (see Elson and Magde, (1974) Biopolymers, 13: 1; Rigler et al., (1992) in *Fluorescence Spectroscopy: New Methods and Applications*, Springer Verlag, pp.13–24; Eigen and Rigler, (1994) *Proc. Natl. Acad. Sci. U.S.A.*, 91:5740; Kinjo and Rigler, (1995), *Nucleic Acids Res.*, 23:1795).

In FCS, a focused laser beam illuminates a very small volume of solution, of the order of $10^{-15}$ liter, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labeled polypeptide will diffuse at a slower rate if it is large than if it is small. Thus, multimerized polypeptides will display slow diffusion rates, resulting in a lower number of fluorescent bursts in any given time frame, while labeled polypeptides which are not multimerized or which have dissociated from a multimer will diffuse more rapidly. Binding of polypeptides according to the invention can be calculated directly from the diffusion rates through the illuminated volume.

Where FCS is employed, rather than FRET, it is not necessary to label more than one binding partner polypeptide. Preferably, a single polypeptide member of the multimer is labeled. The labeled polypeptide dissociates from the multimer as a result of modification, thus altering the FCS reading for the fluorescent label.

A further detection technique which may be employed in the method of the present invention is the measurement of time-dependent decay of fluorescence anisotropy. This is described, for example, in Lacowicz, 1983, *Principles of Fluorescence Spectroscopy*, Plenum Press, New York, incorporated herein by reference (see, for example, page 167). Fluorescence anisotropy relies on the measurement of the rotation of fluorescent groups. Larger multimers of polypeptides rotate more slowly than monomers, allowing the formation of multimers to be monitored.

Fluorescence polarization (FP) can also be used to detect binding or dissociation of binding partner polypeptides. See Lundblad et al., (1996) *Mol. Endocrinol.* 10:607; Nasir et al., (1999) *Comb. Chem. High Throughput Screen.* 2:177. Fluorescently labeled binding partner polypeptides emit light in the same polarized plane when excited with plane polarized light if the molecule remains stationary throughout the excited state. However, the excited molecule can rotate or tumble out of the plane of polarized light during the excited state and emit light in a different plane. Emission light intensity can be monitored in more than one plane. The degree to which emission intensity moves from one plane to another plane is related to the mobility of the fluorescently labeled binding partner polypeptide. Where a fluorescently labeled binding partner polypeptide is bound to its corresponding binding partner, it will move very little during the excited state interval because it is a large molecule, and the emitted light will remain highly polarized with respect to the excitation plane. If a fluorescently labeled binding partner is not bound to its corresponding binding partner it will rotate or tumble faster because it is a small molecule. The resulting emitted light will be depolarized relative to the excitation plane.

A large number of assays can be conceived, based upon the principles outlined above. The principle can be summarized, in this case for phosphorylation, as follows:

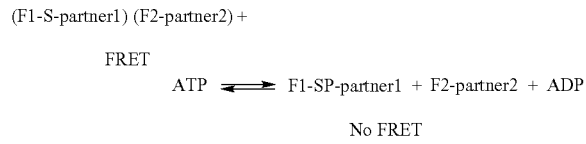

The following alternative assay format also is envisaged:

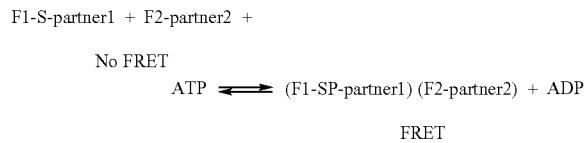

Where S=phosphorylation modification site
P=phosphorylation
F1=donor fluorophore
F2=acceptor fluorophore
FRET=Fluorescent resonance energy transfer Each binding partner polypeptide may be labeled with one or more fluorescent molecules. In order to measure multiple enzyme activities with several different modification dependant binding polypeptides, there are several important criteria for fluorescent labeling. The method must be able to label modification dependant binding polypeptides with different colored fluorescent labels and also must be able to label different modification dependant binding polypeptides specifically. In the solution phase assays, at least two different colored labels are needed for FRET, and multiple colors are necessary to perform multiple FP assays in the same tube. Furthermore, in order to monitor the association of modification dependent binding proteins using FRET or FP, the fluorescent labels must be able to be specifically placed in the correct location and orientation. In an immobilized assay, the potential is greater, modification dependant binding polypeptides can be distinguished both spatially and by color, facilitating the measurement of numerous enzymes at the same time. Predictable label positioning is necessary to maintain the correct binding activity of the modification dependant binding polypeptides.

Green fluorescent proteins ("GFPs") of cnidarians, which act as their energy-transfer acceptors in bioluminescence, can be used in the invention. A green fluorescent protein, as used herein, is a protein that fluoresces green light, a blue fluorescent protein is a protein that fluoresces blue light, and a red fluorescent protein is a protein that fluoresces red light. GFPs have been isolated from the Pacific Northwest jellyfish, *Aequorea Victoria,* from the sea pansy, *Renilla reniformis,* and from *Phialidium gregarium.* (Ward et al., (1982) *Photochem. Photobiol.,* 35:803; Levine et al., (1982) *Comp. Biochem. Physiol.,*72B:77).

A variety of *Aequorea*-related GFPs having useful excitation and emission spectra have been engineered by modifying the amino acid sequence of a naturally occurring GFP from *Aequorea victoria.* (Prasher et al., (1992) *Gene,* 111: 229; Heim et al., (1994) *Proc. Natl. Acad. Sci. U.S.A.,* 91:12501; PCT/US95/14692). As used herein, a fluorescent protein is an Aequorea-related fluorescent protein if any contiguous sequence of 150 amino acids of the fluorescent protein has at least 85% sequence identity with an amino acid sequence, either contiguous or non-contiguous, from the wild-type *Aequorea* green fluorescent protein (SwissProt Accession No. P42212). More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type *Aequorea* green fluorescent protein of SwissProt Accession No. P42212. Similarly, the fluorescent protein may be related to *Renilla* or *Phialidium* wild-type fluorescent proteins using the same standards.

*Aequorea*-related fluorescent proteins include, for example, wild-type (native) *Aequorea victoria* GFP, whose nucleotide and deduced amino acid sequences are presented in Genbank Accession Nos. L29345, M62654, M62653 and others *Aequorea*-related engineered versions of Green Fluorescent Protein, of which some are listed above. Several of these, i.e., P4, P4-3, W7 and W2 fluoresce at a distinctly shorter wavelength than wild type. Blue fluorescent proteins and red fluorescent proteins such as DsRed (Clontech) from Discosoma species and variants and mutants thereof can also be used.

Recombinant nucleic acid molecules encoding single- or tandem fluorescent protein/polypeptide comprising a binding domain and/or a binding partner therefor fused to a fluorescent protein useful in the invention may be expressed either for in vivo assay of the activity of a modifying enzyme on the encoded products. Alternatively, the encoded fusion proteins may be isolated prior to assay, and instead assayed in a cell-free in vitro assay system, as described elsewhere herein.

Non-fluorescent Methods to Detect Protein: Protein Binding

The activity of a modification enzyme can further be assayed by methods of the invention which do not use fluorescently labeled binding partner polypeptides to detect the distance (i.e. binding or dissociation) between binding partner polypeptides. For example, one binding partner can be immobilized on a solid support. The binding partner that is not immobilized can be tagged with for example, a coiled-coil, an antibody, a single chain antibody, an antigen, or biotin. When the tagged binding partner polypeptide is added to the immobilized binding partner polypeptide in the presence of a modifying enzyme the association of the binding partners can be monitored by adding a detector molecule that associates with the tagged portion of the binding partner after washing away any unbound tagged binding partner. If the tagged binding partner has associated or bound to the immobilized binding partner in the presence of the enzyme, then the detector molecule will associate with the tagged binding partner. The detector molecule can then be detected. Detection of the tagged binding partner polypeptide indicates binding of the binding partner polypeptides and the absence of detection indicates no association of binding partner polypeptides.

In another example, a non-immobilized radioactive molecule tagged binding partner polypeptide can be added to an immobilized binding partner polypeptide in the presence of a modifying enzyme. After the washing away of unbound tagged binding partner polypeptides, binding of the binding partner polypeptides can be detected by monitoring the presence or absence of radioactivity. Detection of the radioactive molecule tagged binding partner indicates binding of the binding partner polypeptides and the absence of detection indicates no association of binding partner polypeptides.

Optionally, the binding partner polypeptides can be associated or bound to one another at the beginning of an assay and a modification enzyme can be added in order to monitor the dissociation of the binding partner polypeptides.

Therefore, an assay of the invention can comprise, for example, mixing one or more tagged binding partner polypeptides, one or more preferably immobilized binding partner polypeptides, and one or more protein modifying enzymes. The tagged binding partner polypeptides or the immobilized binding partner polypeptides comprise one or more sites for the modifying enzyme to act upon wherein modification of the protein promotes binding or dissociation of the binding partner polypeptides from or to the corresponding tagged binding partners. The binding partners are mixed under conditions which permit binding of the binding partner polypeptides with the tagged binding partners. The binding or dissociation of the binding partner polypeptides is then detected. Detection of binding or dissociation as a result of said mixing is indicative of enzyme activity.

A Kit for Assaying the Activity of a Protein-Modifying Enzyme

In order to facilitate convenient and widespread use of the invention, a kit is provided which contains the essential components for screening the activity of an enzyme which mediates a change in protein modification, as described above. Binding partner polypeptides which bind or dissociate in a modification-dependent manner are provided, as is a suitable reaction buffer for in vitro assay or, alternatively, cells or a cell lysate. Preferably, one or both of the binding partner polypeptides comprise one or more tags. Preferably, a binding partner polypeptide comprising a binding domain is immobilized on a solid support. Even more preferably, the immobilized binding partner polypeptide is unlabeled. Optionally, a detector molecule is provided.

A reaction buffer which is "suitable" is one which is permissive of the activity of the enzyme to be assayed and which permits modification dependent binding of the binding partners. The labeled components are provided as peptide/protein or a nucleic acid comprising a gene expression construct encoding the one or more of a peptide/protein. Polypeptides in a kit of the invention are supplied either in solution (preferably refrigerated or frozen) in a buffer which inhibits degradation and maintains biological activity, or are provided in dried form, i.e., lyophilized. In the latter case, the components are resuspended prior to use in the reaction buffer or other biocompatible solution (e.g. water, containing one or more of physiological salts, a weak buffer, such as phosphate or Tris, and a stabilizing substance such as glycerol, sucrose or polyethylene glycol); in the latter case, the resuspension buffer should not inhibit modification-dependent protein binding when added to the reaction buffer in an amount necessary to deliver sufficient protein for an assay reaction. Polypeptides provided as nucleic acids are supplied- or resuspended in a buffer which permits either transfection/transformation into a cell or organism or in vitro transcription/translation. Each of these components is supplied separately contained or in admixture with one or more of the others in a container selected from the group that includes, but is not limited to, a tube, vial, syringe or bottle.

An enzyme being assayed according to the invention is added to the assay system either as a protein (isolated, partially-purified or present in a crude preparation such as a cell extract or even a living cell) or a recombinant nucleic acid. Methods of expressing a nucleic acid comprising an enzyme or other protein are well known in the art.

An assay of the invention is carried out using the kit according to the methods described above and elsewhere herein.

Methods of Screening for a Candidate Modulator of Enzymatic Activity

A candidate modulator of activity of a protein-modifying enzyme can be assayed according to the invention and is determined to be effective if its use results in a difference of at least 5%, 10%, 20%, 30%, 40%, 50%, or greater relative to controls in which it is not present in FRET or other signal emanating from a detectable label of use in the invention resulting from the association of binding partner polypeptides in the presence of a protein-modifying enzyme.

Modulation refers to the capacity of a modulator to either increase or decease a measurable functional property of biological activity or process (e.g., enzyme activity or receptor binding) by at least 10%, 15%, 20%, 25%, 50%, 100% or more compared to controls where the modulator is not present. An increase or decrease may be contingent on the occurrence of a specific event, such as activation of a signal transduction pathway, and/or may be manifest only in particular cell types. Modulation may be direct (e.g. including, but not limited to, cleavage of- or competitive binding of another substance to the enzyme) or indirect (e.g. by blocking the initial production or, if required, activation of the modifying enzyme).

A modulator is a biological or chemical agent which modulates the activity of an enzyme by enhancing or inhibiting the activity of an enzyme and can be naturally occurring or non-naturally occurring, such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown, or partially-known. Such modulators can be screened using the methods described herein.

A candidate modulator is a compound to be tested by one or more screening method(s) of the invention as a putative modulator. Usually, various predetermined concentrations are used for screening such as 0.01 µM, 0.1 µM, 1.0 µM, and 10.0 µM. Test compound controls can include the measurement of a signal in the absence of the test compound or comparison to a compound known to modulate the target.

Whether in vitro or in an in vivo system, the invention encompasses methods to screen compositions which may enhance, inhibit or not affect (e.g., in a cross-screening procedure in which the goal is to determine whether an agent intended for one purpose additionally affects general cellular functions, of which protein modification is an example) the activity of a protein-modifying enzyme.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 500 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoal antigens, and parasitic antigens. Candidate modulators additionally comprise proteins, lipoproteins, glycoproteins, phosphoproteins, and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens, and antibodies.

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target mRNA. Ribozymes of the hammerhead class are the smallest known, and lend themselves both to in vitro production and delivery to cells (summarized by Sullivan, (1994) *J. Invest. Dermatol.*, 103:85S; Usman et al., (1996) *Curr. Opin. Struct. Biol.*, 6:527).

As stated above, antibodies are of use in the invention as modulators (specifically, as inhibitors) of protein-modifying enzymes. Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit, or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal Antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., (1992) *J. Biol. Chem.*, 267:4815). The serum is titered against protein antigen by ELISA or alternatively by dot or spot blotting (Boersma and Van Leeuwen, (1994) *J. Neurosci. Methods*, 51:17). At the same time, the antiserum may be used in tissue sections prepared as described below. The serum is shown to react strongly with the appropriate peptides by ELISA, for example, following the procedures of Green et al., (1982) *Cell*, 28:477.

2. Monoclonal Antibodies.

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., (1981) *Nature*, 294:278.

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab, or F(ab')$_2$ fragment or a derivative thereof, such as a single chain Fv fragment. The antibody or antibody fragment may be non-recombinant, recombinant, or humanized. The antibody may be of an immunoglobulin isotype, e.g., IgG, IgM, and so forth. In addition, an aggregate, polymer, derivative, and conjugate of an immunoglobulin or a fragment thereof can be used where appropriate.

The level of activity of a candidate modulator may be quantified using any acceptable limits, for example, via the following formula:

$$\text{Percent Modulation} = \frac{(\text{Index}_{Control} - \text{Index}_{Sample})}{(\text{Index}_{Control})} \times 100$$

where Index$_{control}$ is the quantitative result (e.g., amount of- or rate of change in fluorescence at a given frequency, rate of molecular rotation, FRET, rate of change in FRET or other index of modification, including, but not limited to, enzyme inhibition or activation) obtained in assays that lack the candidate modulator (in other words, untreated controls), and Index$_{sample}$ represents the result of the same measurement in assays containing the candidate modulator. As described herein, control measurements are made with a differentially-labeled binding domain and its corresponding partner only and with these molecules plus a protein-modifying enzyme which recognizes a site for post-translational protein modification present on the binding domain and, optionally, on the binding partner.

The invention provides a method of screening for a candidate modulator of enzymatic activity of, for example, one or more of the following enzymes: a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase), an NAD:Arginine ADP ribosyltransferase, and a protease. The method comprises contacting a binding partner polypeptide, which is preferably immobilized on a solid support, a binding partner therefor and an enzyme with a candidate modulator of the enzyme, wherein at least one binding partner polypeptide comprises a binding domain that includes a site for modification and binds the binding partner in a manner that is dependent upon modification of the site by the enzyme. At least one of the binding partner polypeptides comprises a detectable label and optionally both the isolated binding partners comprise at least one label. Binding of the binding partners is monitored, wherein binding or dissociation of the binding partners as a result of the contacting is indicative of modulation of enzymatic activity by the candidate modulator of the enzyme. Preferably, enzyme activity is also measured in the absence of the candidate modulator and this level of activity is compared to the level of activity in the presence of the candidate modulator.

A Kit for Screening a Candidate Modulator of Protein-modifying Enzyme Activity

A candidate modulator of enzymatic modification may be assayed using a kit of the invention. A kit as described above is used for this application, with the assay performed further comprising the addition of a candidate modulator of a modifying enzyme which is present in the reaction system. Optionally, a protein-modifying enzyme is supplied with the kit, either as a protein or nucleic acid as described above.

Assays of protein activity are performed as described above. At a minimum, three detections are performed, one in which the binding partner polypeptides are present without the modifying enzyme or candidate modulator thereof (control reaction A), one in which the same polypeptide components are incubated with the modifying enzyme under conditions which permit the modification reaction to occur (control reaction B) and one in which the modifying enzyme and candidate modifier are both incubated with binding partner polypeptides under conditions which permit the modification reaction to occur (test reaction). The result of the last detection procedure is compared with those of the first two controls; the candidate inhibitor is judged to be efficacious if there is a shift in either of the observed amount of FRET or the rate at which FRET changes or, alternatively, of another index of fluorescence, such as monomer/excimer fluorescence, fluorescence correlation spectroscopy (FCS), FP, or fluorescence anisotropy, or another index of reporting of at least 5, 10, 20, 30, 40, 50% or more, away from that observed in control reaction B toward that observed in control reaction A.

The following are provided for exemplification purposes only and are not intended to limit the scope of the invention described in broad terms above. All references cited in this disclosure are incorporated herein by reference.

EXAMPLES

Example 1

Figure 1:
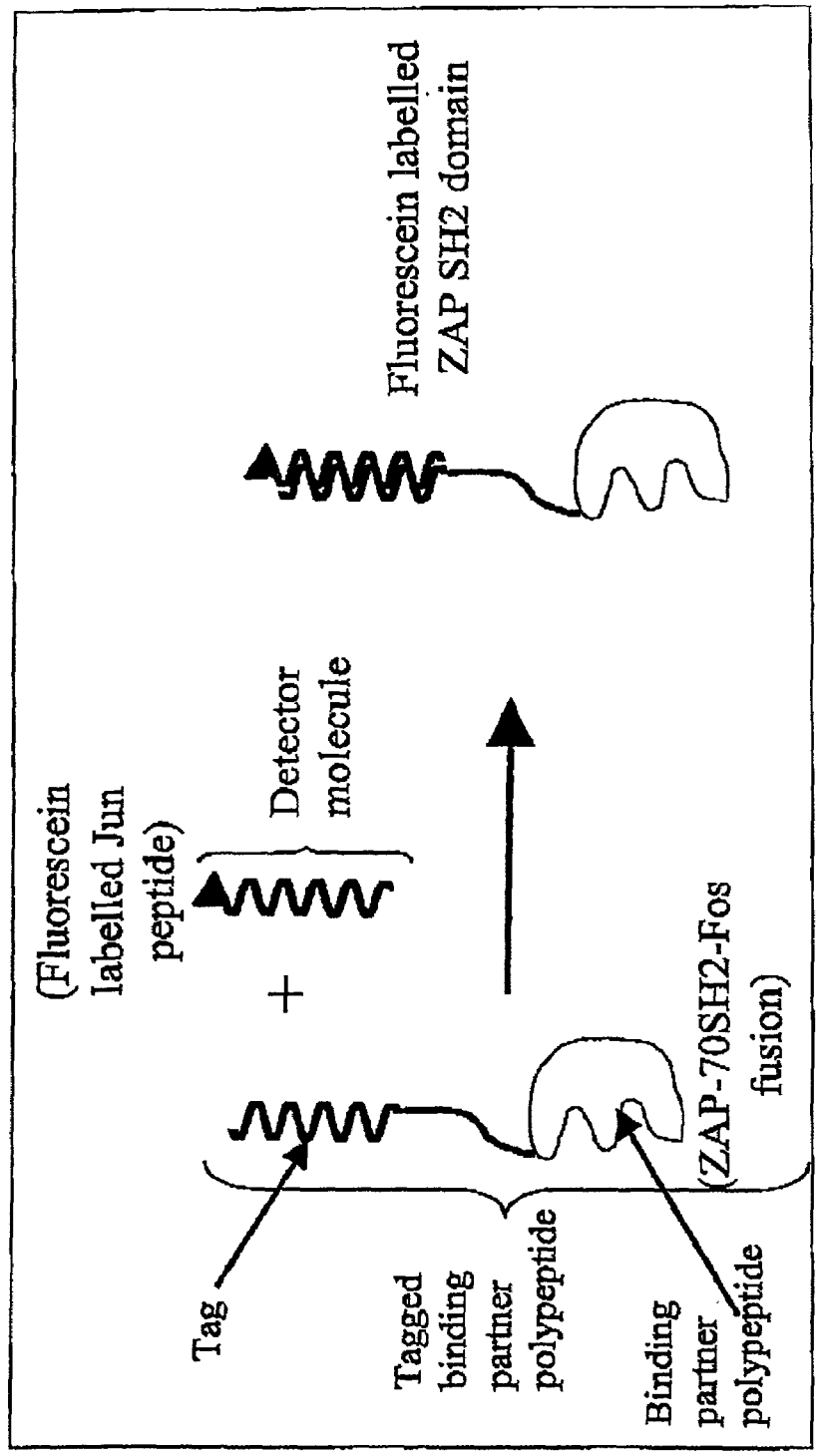

Measurement of Src Protein Kinase and Yersinia Phosphatase Activities by the Modulation of FRET Between Binding Partners Labeled with Fluorescent Coiled-coil Heterodimers This example is based on the concept of using heterodimeric peptides as tools to enable specific fluorescent labeling of protein domains. The example describes the use of coiled-coil heterodimers to attach fluorescent labels to protein domains in such a way that binding of the proteins to each other results in FRET between the fluorophores. See FIG. 1.

The binding partner domains in this example are the SH2 domain of ZAP70 kinase and the zeta chain of the T-cell receptor peptide. The SH2 domain of ZAP70 and the T-cell receptor Zeta chain peptide are able to bind together when the T-cell receptor is phosphorylated by Src or Fyn kinase. This example illustrates the attachment of chemical fluorophores to these binding partners using coiled-coil heterodimers.

DNA Constructs a) ZAP70-FJ Peptide

The ZAP70SH2 domain was constructed as a fusion protein derived from the natural Fos/Jun coiled-coil domains. Oligonucleotides derived from the coiled-coil domain of Fos/Jun were designed and synthesized:

Forward primer:

```
Forward primer:
GGGGGGAGCTCTGGGAGGCGGAGGTGGAGGGCTGATGCGCCAGCTGCAGGATGAAG    (SEQ ID NO:31)
TTGAAGAACTGGAACAGGAAAACTGGCATCTGCAGA Reverse primer
CCCCCCTCGAGTTATTAAACTTCGGCTTCCAGGCACTGAACTTCACGCAGCAGACGG   (SEQ ID NO:31)
GCAACTTCGTTCTGCAGATGCCAGTTTTCCTGTTCCAGT
```

This DNA contains SacI and XhoI sites for cloning purposes and encodes a glycine linker followed by the coiled-coil polypeptide sequence and two stop codons (Polypeptide FJ):

L M R Q L Q D E V E E L E Q E N W H L Q N E V A R L L R E V Q C L E A E V (SEQ ID NO:33).

The primers were annealed together by heating to 96° C. followed by slow cooling to room temperature. Complete double stranded DNA was generated by "filling in" the single stranded 5' overhangs using Klenow fragment of DNA polymerase I (NEB). The DNA fragment was purified by electrophoresis in 1.2% agarose gel and DNA was extracted from an isolated gel band using Qiagen spin columns. The purified fragment was digested with SacI and XhoI and purified as above prior to ligation into the bacterial expression vector pET28a (Novagen) to generate vector FS101. FS101 was then digested with NheI and EcoRI and DNA encoding ZAP70SH2 domain (from FS44) was ligated into this plasmid to generate vector FS102 that is designed to express ZAP70-FJ.

The corresponding synthetic Fos/Jun polypeptide partner that forms the coiled-coil pair with ZAP70-FJ was designed and prepared:

Peptide 1: R M R Q L E D R V E E L R E Q N W
H L A N Q V A R L R Q R V C E L K A R V
(SEQ ID NO:34).

b) 4HA-TCRζ

Oligonucleotides based on the coiled-coil domains that are optimized derivatives of molecular velcro (REF) were designed and synthesized:

```
Forward primer:
GTACCGCTAGCTCTTACAAGGGTATTGCTCAGTTGGAGCAGGAAATCGCC    (SEQ ID NO:35).
CAATTAGAACAAGAAAATGCACAACTTGAA Reverse primer:
GGGCATCGATTTCCTGCTCAAGCTGAGCGATCTCTTGTTCAAGTTGTGCAT   (SEQ ID NO:36).
TTTCTTGTTCTAATTGGGCGAT
```

This DNA contains NheI and ClaI sites for cloning purposes and encodes the corresponding polypeptide sequence (Polypeptide 4HA):

Y K G I A Q L E Q E I A Q L E Q E N A Q L E Q
E I A Q L E Q E (SEQ ID NO:37).

The primers were annealed together by heating to 96° C. followed by slow cooling to room temperature. Complete double stranded DNA was generated by "filling in" the single stranded 5' overhangs using Klenow fragment of DNA polymerase I (NEB). The DNA fragment was purified by electrophoresis in 1.2% agarose gel and DNA was extracted from an isolated gel band using Qiagen spin columns. The purified fragment was digested with NheI and ClaI and purified as above prior to ligation into the plasmid FS19 to generate vector FS103. FS103 was then digested with NheI and BamHI and DNA encoding the 4HA-TCRζ was ligated into pET28a to generate a bacterial expression vector FS104.

The corresponding synthetic 5HB polypeptide partner that forms the coiled-coil pair with 4HA-TCRζ was designed and prepared:

Polypeptide 5HB:

Y K G I C Q L R Q R I A Q L R Q R N A Q L R
Q R I A Q L R Q R I A Q L R Q R (SEQ ID NO:38).

An additional synthetic peptide (peptide 3) was designed and chemically synthesised. This peptide corresponded to residues 52–87 of TCRζ and is known to bind to ZAP70. This peptide was to be used for immobilization assays, or for solution based assays in place of the cloned TCR zeta chain:

Peptide 3 RCKFSRSAEPPAYQQGQNQLYNELN-
LGRREEYDVLD (SEQ ID NO:39).

Expression and Purification Procedure

Fresh transformants of Zap70-FJ pET-28a in BRL(DE3) and 4HA-TCR pET-28a in BRL(DE3) pLysS were used to inoculate 3ml LB/kanamycin (100 µg/ml). The starter cultures were incubated overnight at 37° C. with shaking. From these starter culturess 1 ml was used to inoculate 400 ml TB/kanamycin (100 µg/ml) in a 2L, baffled flask. Cultures were incubated at 37° C. at 200 rpm for approximately 5 hrs until the O.D. 600 nm had reached 0.5 Abs units. At this point cultures were induced by adding IPTG to a concentration of 1 mM. The cultures were then left incubating at room temperature overnight with gentle shaking on a benchtop shaker.

Bacteria were harvested by centrifugation at 3000 rpm for 20 mins. The bacterial pellet was resuspended in 25 ml lysis buffer (50 mM Pi pH 7.0, 300 mM NaCl, 2% Proteinase inhibitor cocktail, 0.75 mg/ml Lysozyme). Lysis of the resuspended cells was initiated by gentle stirring on a stirrer plate for 1 hr at room temperature. The partially lysed mixture was subjected to 2 cycles of freeze thawing in liquid nitrogen. Finally, the cells were sonicated on ice using a 10 mm probe at high power. Sonication was performed on a pulse setting for a period of 3 min. The crude lysate was then centrifuged at 15000 rpm for 30 mins to remove cell debris. HIS tagged proteins were purified from the clear lysate using Talon resin (Clontech). Proteins were bound to the resin in a batchwise manner by gentle shaking at room temperature for 30 min. Non-HIS tagged proteins were removed by washing the resin at least twice with 10×bed volume of wash buffer (50 mM Pi pH 7.0, 300 mM NaCl, 5 mM fluorescence-blank Imidazole ). The washed resin was loaded into a 2 ml column and the bound proteins released with elution buffer (50 mM Pi pH 7.0, 300 mM NaCl, 150 mM florescence-blank imidazole). Elution was normally achieved after the first 0.5ml and within 2–3ml in total. Proteins were stored at −80° C. after snap freezing in liquid nitrogen in the presence of 10% glycerol.

Fluorescent Labeling Procedure

Peptide domains can be specifically labeled on amine or thiol groups with chemical fluorophores such as fluorescein or rhodamine. Fluorophores with thiol or amine reactive chemistries are readily available from commercial sources such as Molecular Probes. These fluorophores can be conjugated to peptides under mild conditions (e.g. 20 mM TES pH 7 for thiol directed labeling, or 200 mM sodium bicarbonate pH 8.3 for amine directed labeling, using 200 µM to peptide in the presence of 200 µM label).

Figure 2:
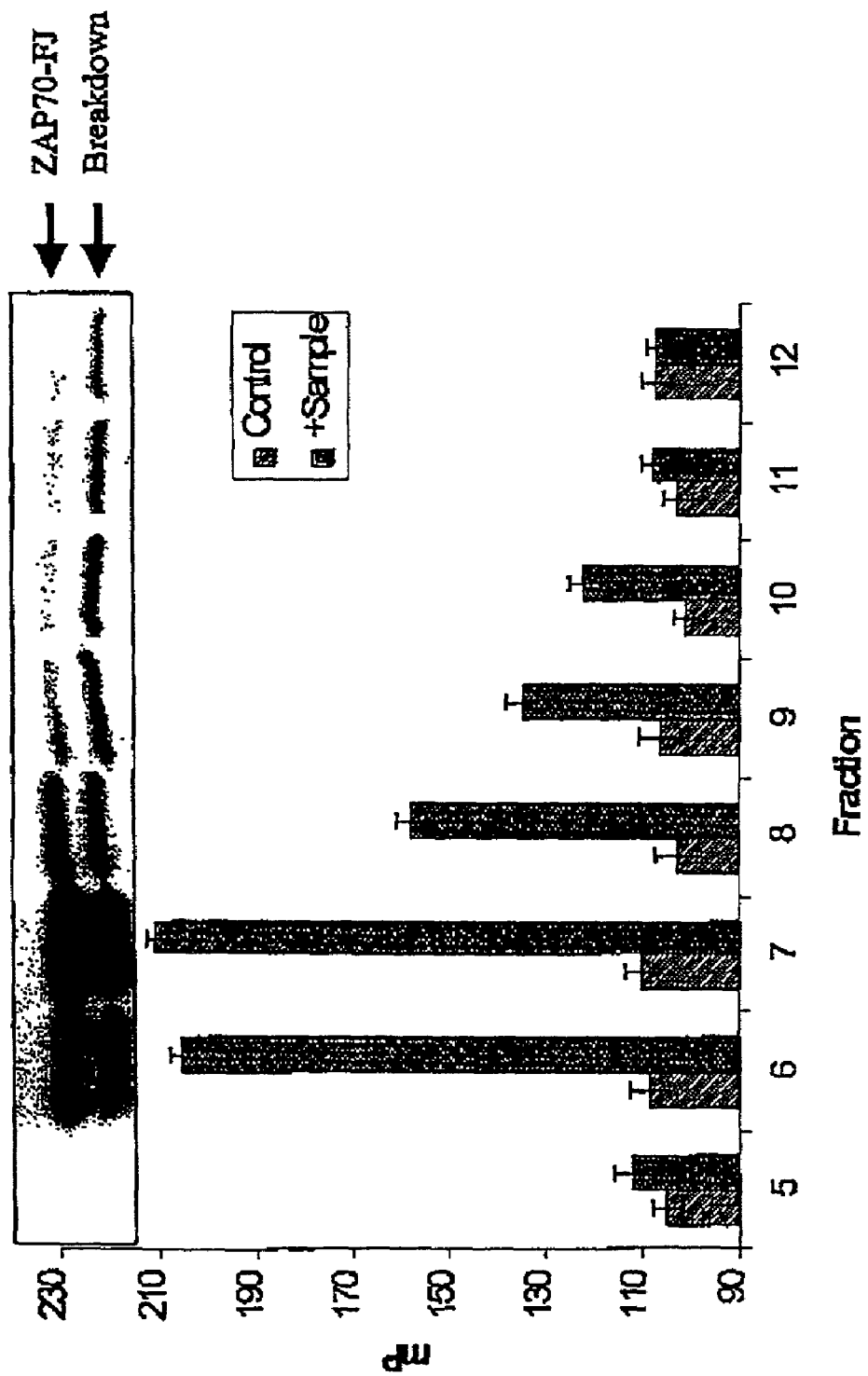

One half of a Fos/Jun based coiled-coil heterodimer pair (peptide 1) was labeled with fluorescein. The labeled peptide was incubated in a microtitre plate, at 30° C., at a final concentration of 1 µM in 50 mM sodium phosphate pH 7.0. Fractions from a purification of ZAP70-FJ were added (20 µl, to a final volume of 100 µl), and the fluorescence polarisation (ex. 485 nm, em 520 nm) followed over time. For control samples the same volume of 50 mM sodium phosphate pH 7.0, 300 mM NaCl and 150 mM imidazole (elution buffer) was added to the well. FIG. 2 depicts the final fluorescent polarisation value obtained for each fraction.

Solution Phase FRET Assay for Src Tyrosine Kinase

Figure 4:
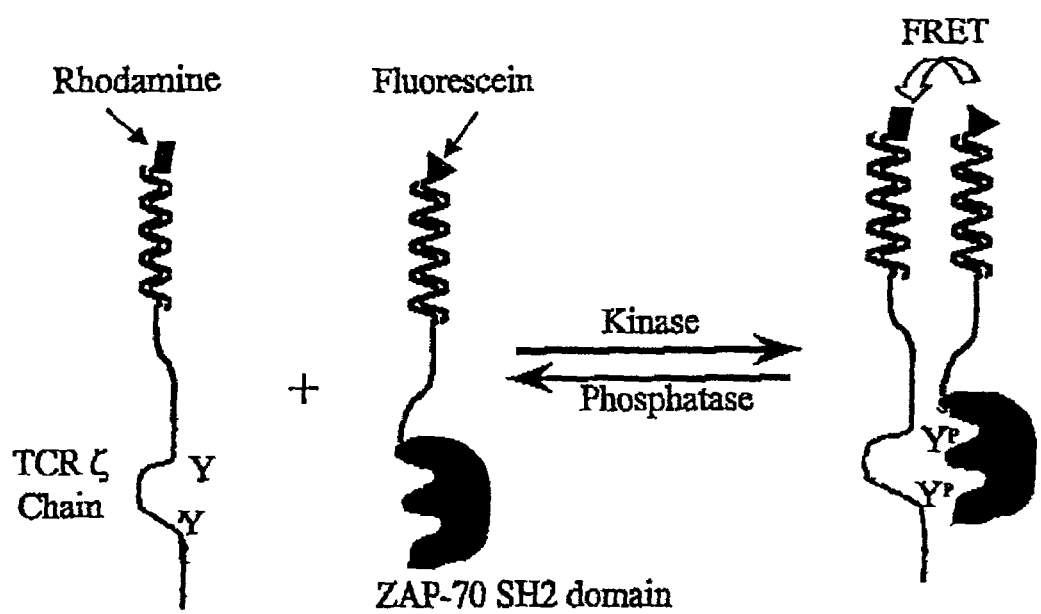
FIG. 4 shows a schematic of ZAP70 and TCR binding reaction with 2 different heterodimeric coiled-coil based fluorescent tags.

In a similar way to the ZAP labeling procedure, the TCR zeta chain domain fused to the 4HA coiled-coil peptide can be labeled with a 5HB peptide carrying rhodamine. The two binding domains, ZAP70 and TCR, labeled with fluorescein and rhodamine respectively, can be used to monitor the activities of kinases or phosphatases acting to phosphorylate or dephosphorylate the TCR zeta chain. An SH2 domain labeled with fluorescein can interact with phosphorylated TCRζ chain labeled with rhodamine. The fluorophores will then be close enough for FRET to occur between fluorescein and rhodamine (see FIG. 4). Rhodamine will accept energy from fluorescein when in close proximity resulting in a loss of emission from the fluorescein that can be followed using a fluorimeter or fluorescent microtitre plate reader such as the BMG Polarstar Galaxy.

SH2 and TCR domains can be mixed in a suitable buffer (e.g. 20 mM Tris-HCl pH 7.2, 1 mM ATP, 10 mM MgCl$_2$, 0.04 mM EDTA, 0.003% (v/v) Brij 35, 0.04mg/ml BSA, 0.08% (v/v) β-mercaptoethanol). Src enzyme can be added to start the reaction. Phosphorylation of the TCR zeta chain is followed by the change in fluorescein quench due to FRET.

Alternatively, ZAP70-labeled with fluorescein via the FJ coil can be used with a chemically labeled synthetic TCR peptide coupled to rhodamine, and enzyme activity monitored again by acceptor gain or donor loss in FRET.

Solution Phase FRET Assay for Tyrosine Phosphatases

Measurement of phosphatase activity can be shown using a phosphatase, YOP from *Yersinia pestis*, (Upstate Biotechnologies). Phosphatase activity can be detected with the ZAP70 labeled with FJ peptide-fluorescein and a rhodamine labeled peptidic mimic of the phosphorylated TCRζ chain:

(RCKFSRSAEPPAYQQGQNQLY$_{(p)}$NELNLGR-
REEY$_{(p)}$DVLD) (SEQ ID NO:40) labeled with
rhodamine at the thiol position.

Reactants can be mixed in a suitable buffer (e.g. 50 mM Tris-HCl pH 7.4 including 150 mM NaCl and 0.2%(v/v) Tween 20) and allowed to equilibrate. Interaction will occur only between the phosphorylated peptide and the SH2 domain, bringing the fluorophores close enough for FRET to occur. The unphosphorylated peptide will not bind to the SH2 domain. Addition of the phosphatase will disrupt the interaction by removing the phosphate moieties, thereby reducing FRET.

Example 2

Measurement of Src Protein Kinase and Yersinia Phosphatase Activity using an Immobilized Assay using Binding Partners Labeled with Fluorescent Coiled-coil Heterodimers The interaction of the natural binding domains can also be followed if the partner modified by the enzyme is immobilized on a suitable surface, (e.g. through a biotin:avidin interaction or a His-Tag:Ni/NTA interaction). The assay can then be adapted to an endpoint assay format where excess incoming binding partner can be washed away. The assay requires that only one of the interacting partners be labeled with a fluorophore, the other labeled with a suitable anchoring moiety. The assay can be used to determine inhibitors of the binding interaction or of the phosphatase/kinase involved in mediating the interaction.

Immobilized Tyrosine Phosphatase Assay

A phosphorylated peptide mimicking the critical structure of the TCRζ chain can be biotinylated and bound to a commercially available microtitre plate pre-coated with streptavidin (Pierce), under mild conditions (e.g. 2.3 µM peptide in TBS containing 0.2% Tween 20 and 1% BSA). A non-phosphorylated analogue can be included as a control. The peptide bound to the plate can then be treated with a phosphatase under suitable conditions (e.g. 25 mM Tris-HCl pH 7.2, 5 mM EDTA 10 mM β-mercaptoethanol, 50 µg/ml BSA). Alternatively, the peptide can be reacted with the phosphatase prior to its binding to the streptavidin-coated plate. An SH2 domain can be used to detect the phosphorylation status of the peptide on the plate. This SH2 domain can be fluorescently labeled with FJ peptides coupled to fluorescein as for the solution phase assay. The SH2 domain can be applied in mild conditions such as PBST/BSA or other suitable buffer. Phosphate dependent binding can be determined after washing off excess probe and reading in a suitable instrument.

Immobilized Src Tyrosine Kinase Assay

Src protein kinase activity can be determined by measuring the transfer of phosphate groups to immobilized binding partner substrates.

Src Kinase Assay with Nickel/NTA Immobilized TCRζ Chain

A TCRζ chain can be expressed and purified with a hexapeptide comprised of histidine residues to facilitate anchoring the protein to a microtitre plate coated with a nitrilotriacetic acid surface, (Pierce). Immobilization of the domain can be achieved simply by incubating the domain on the plate under suitable conditions (e.g. 50 mM phosphate pH 7, 300 mM NaCl, 5mM imidazole). Excess protein can be washed off with the binding buffer including 0.2% (v/v) Tween 20. The immobilized substrate can then be reacted with the tyrosine kinase under suitable reaction conditions (e.g. 20 mM Tris-HCl pH 7.2, 1 mM ATP, 10 mM MgCl$_2$, 0.04 mM EDTA, 0.003% (v/v) Brij 35, 0.04 mg/ml BSA, 0.08% (v/v) β-mercaptoethanol). Phosphorylated TCRζ chain can be detected using an SH2 domain fluorescently labeled with fluorescein as in example 1.

Src Kinase Assay with Biotin/Streptavidin Immobilized TCRζ Chain,

Alternatively, the synthetic TCR zeta peptide, peptide 3, can be immobilized using a biotin:streptavidin interaction. The peptides can be biotinylated under mild conditions using amine or thiol directed chemistry (e.g. 20 mM TES pH 7 for thiol directed labeling, and 200 mM sodium bicarbonate pH 8.3 for amine directed labeling, using 230 μM peptide in the presence of 200 μM label). Biotinylated peptides can be bound to a streptavidin-coated plate prior to the kinase reaction, or alternatively, can be phosphorylated prior to binding.

```
Forward primer  GGGATCCATATGCCAGACCCCGCGGCGCACCTG   (SEQ ID NO:41)

Reverse Primer  GGAATTCGGGCACTGCTGTTGGGGCAGGCCTCC   (SEQ ID NO:42)
```

Figure 3:
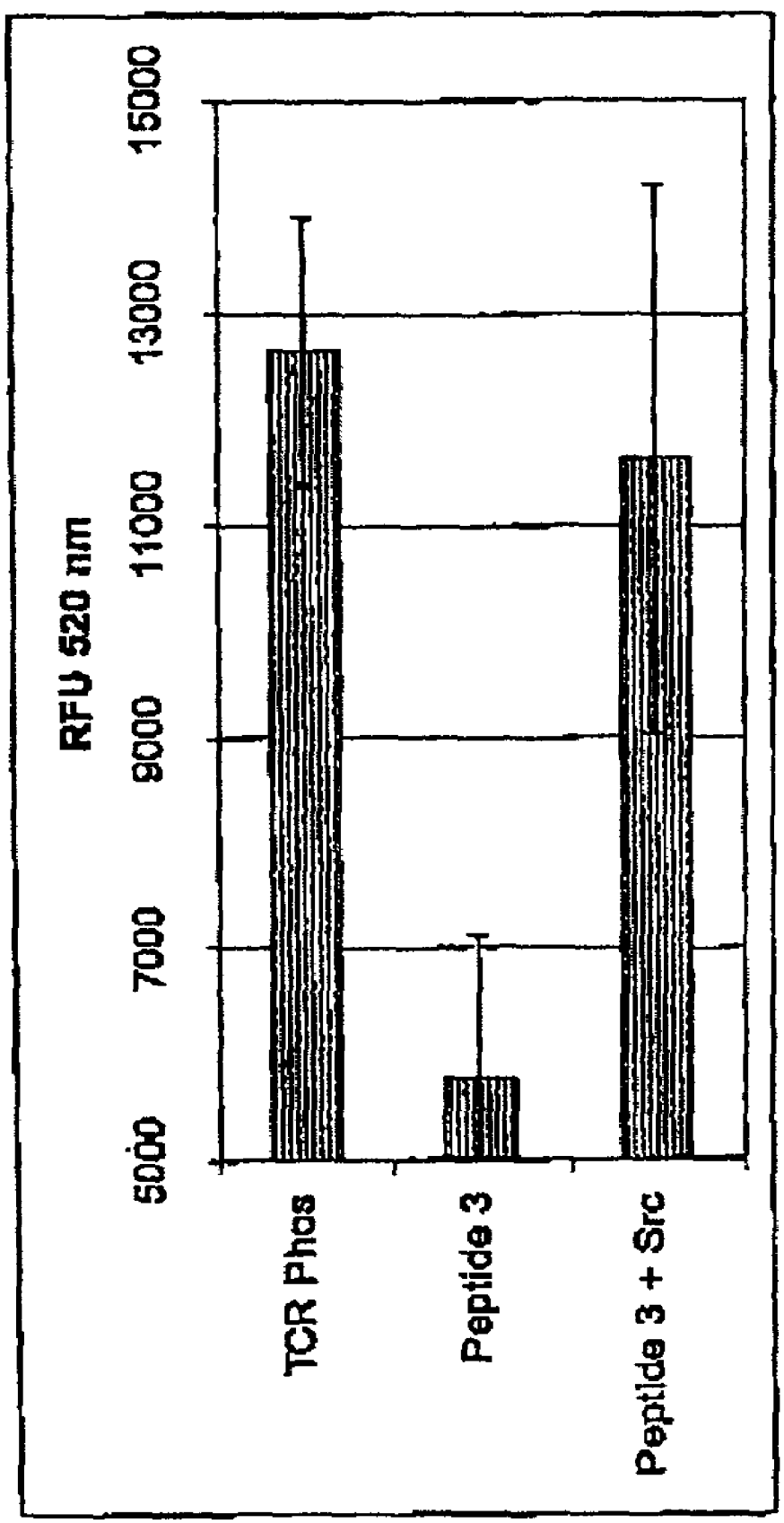
FIG. 3 shows the detection of Src phosphorylation of peptide 3 using ZAP70-FJ labeled with fluorescein.

For example, biotinylated peptide 3 was immobilized using 200 μl of 1 μg/ml peptide per well for 1 hour at room temperature in TBS containing 0.2% Tween 20 (TBST) and 1% BSA. A phosphorylated analogue (TCR-Phos) was used as a positive control and an empty well or peptide without enzyme as negative controls. The peptide bound to the plate was then treated with Src kinase (0.75 units) for 45 minutes at 37° C. in kinase buffer (20 mM Tris-HCl pH 7.2, 1 mM ATP, 10 mM MgCl$_2$, 0.04mM EDTA, 0.003% (v/v) Brij 35, 0.04 mg/ml BSA, 0.08% (v/v) β-mercaptoethanol). Enzyme was washed away using TBST and phosphorylation detected with 70 μl of a 1 in 10 dilution (in TBST+1% BSA) of fluorescein labeled ZAP70-FJ from Fraction 7 of the purification (shown in FIG. 2). The ZAP70 was allowed to bind for 30 minutes at room temperature. The wells were then washed twice with 200 μl of TBST. Fluorescence due to the bound, fluorescein labeled ZAP70-FJ was measured (ex. 485 nm, em 520 nm) and the buffer only background subtracted from each sample. (see FIG. 3).

Example 3

Measurement of Src Protein Kinase and Yersinia Phosphatase Activity by the Modulation of FRET between Binding Partners Labeled with Fluorescent Proteins In order to monitor the association of modification dependent binding proteins using FRET or FP, the fluorescent labels must be in the correct location and orientation. One method of adding fluorescent labels to a predictable site on the protein, and controlling their distance and orientation is through the use of proteinaceous fluorophores such as green fluorescent protein, GFP. GFP and mutants of this protein fluoresce at a variety of different wavelengths, and pairs of fluorescent proteins suitable for FRET can be used.

Modification dependant binding partner polypeptides can be labeled by cloning them into bacterial expression vectors and expressing them as fusion proteins with GFP or a GFP mutant. The following example describes the use of GFP and blue fluorescent protein (BFP) to label modification dependant binding partner polypeptides for the assay of Src kinase and YOP phosphatase.

DNA Constructs a. ZAP-GFP

Primers were designed based on the published ZAP-70 DNA sequence (Genbank accession number L05148). The SH2 domain (amino acids 1–259) of ZAP70 was cloned by PCR using the following oligo-nucleotides:

The resultant PCR fragment was digested with BamHI and EcoRI and inserted into pQBI25-fN1 (Quantum) in order to generate a construct that is designed to express a ZAP70-GFP fusion protein (pFS44).

b. BFP-TCRζ

Primers can be designed based on the published T-cell receptor Zeta chain DNA sequence (Genbank accession number J04132). Three different lengths of the TCR can be cloned by PCR (corresponding to residues 52–163, 60–163 & 69–163) using the following oligo-nucleotides:

```
Forward primer 1   GGGGGCCCAGAGTGAAGTTCAGC    SEQ ID NO:43

Forward primer 2   GGGGGCCCGAGCCCCCGCGTAC     SEQ ID NO:44

Forward primer 3   GGGGGCCCAACCAGCTCTATAAC    SEQ ID NO:45

Reverse Primer     GGGGATCCGCGAGGGGGCAGGGC    SEQ ID NO:46
```

The resultant PCR fragment can be digested with ApaI and BamHI and inserted into pQBI50-fN1 (Quantum) in order to generate a construct that is designed to express the BFP- TCRζ-0 fusion proteins (pFS17 TCR 52–163; pFS18 TCR 60–163; pFS19 TCR 69–163).

Expression and Purification Procedure

Zap-GFP and BFP-TCRζ can be expressed and purified as described previously in example 1.

Solution Phase FRET Assay for Src Tyrosine Kinase

Figure 5:
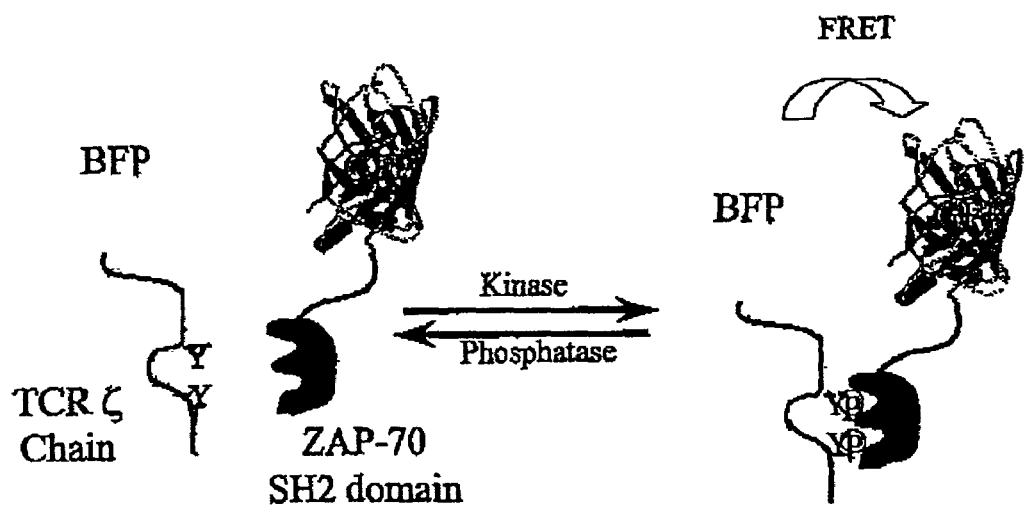
FIG. 5 shows a schematic of ZAP70 and TCR binding reaction with proteinaceous fluorophores.

The two binding domains, ZAP70 and TCR, labeled with GFP and BFP respectively, can be used to monitor the activity of kinases or phosphatases acting to phosphorylate or dephosphorylate the TCR zeta chain. The ZAPSH2-GFP will interact with phosphorylated BFP-TCRζ chain. The binding interaction between ZAPSH2 and TCRζ will bring GFP and BFP close enough for FRET to occur (see FIG. 5). GFP will accept energy from BFP when in close proximity resulting in a gain of emission from the GFP when the BFP is excited. This can be followed using a fluorimeter or fluorescent microtitre plate reader such as the BMG Polarstar Galaxy.

SH2 and TCR domains can be mixed in a suitable buffer (e.g. 20 mM Tris-HCl pH 7.2, 1 mM ATP, 10 mM MgCl$_2$, 0.04mM EDTA, 0.003% (v/v) Brij 35, 0.04mg/ml BSA, 0.08% (v/v) β-mercaptoethanol). Addition of Src enzyme can start the reaction. Phosphorylation of the TCR zeta chain is followed by the change in FRET.

Solution Phase FRET Assay for Tyrosine Phosphatases

Measurement of phosphatase activity can be shown using a phosphatase, YOP from *Yersinia pestis,* (Upstate Biotechnologies). Phosphatase activity is detected with the ZAPSH2-GFP and a peptidic mimic of the phosphorylated TCRζ chain (peptide 6):

(RCKFSRSAEPPAYQQGQNQLY$_{(p)}$NELNLGR-
REEY$_{(p)}$DVLD) (SEQ ID NO:47)

labeled with rhodamine at the thiol position.

Figure 6:
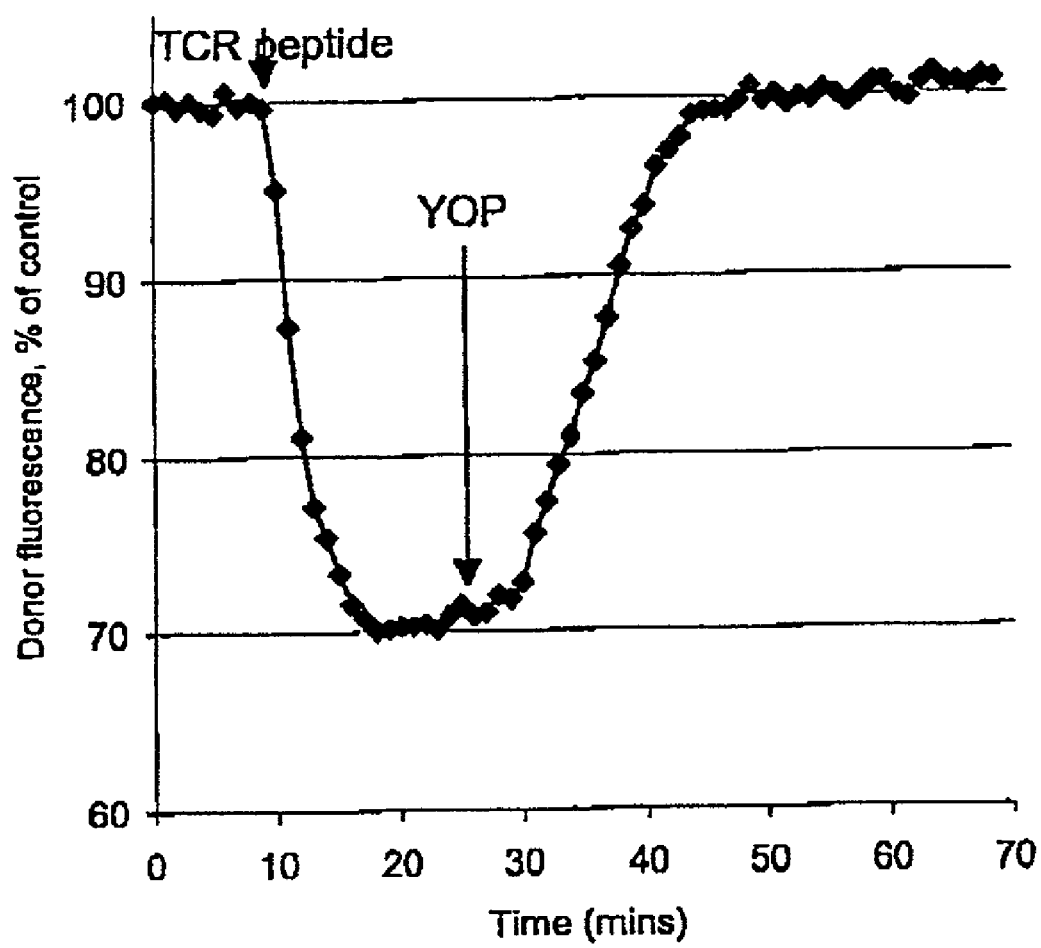
FIG. 6 shows the time course showing dephosphorylation of phosphorylated TCR peptide (Peptide 6) by YOP. The assay is performed in solution, and the increase in donor fluorescence as FRET between the rhodamine labeled peptide and the GFP labeled ZAP domain decreases due to phosphatase action.

Reactants were mixed in a suitable buffer (e.g. 50 mM Tris-HCl pH 7.4 including 150 mM NaCl and 0.2%(v/v) Tween 20) and allowed to equilibrate. Interaction occurs only between the phosphorylated peptide and the SH2 domain, bringing the fluorophores close enough for FRET to occur. The unphosphorylated peptide does not bind to the SH2 domain. Addition of the phosphatase disrupts the interaction by removing the phosphate moieties, thereby reducing FRET. This is shown in FIG. 6.

Example 4

Measurement of Src Protein Kinase and Yersinia Phosphatase Activity using an Immobilized Assay with Binding Partners Labeled with Fluorescent Proteins The interaction of the natural binding domains can also be followed if the partner modified by the enzyme is immobilized on a suitable surface, (e.g. through a biotin:avidin interaction or a His-Tag:Ni/NTA interaction). The assay can then be adapted to an endpoint assay format where excess incoming binding partner can be washed away. The assay requires that only one of the interacting partners be labeled with a fluorophore, the other labeled with a suitable anchoring moiety. The assay can be used to determine inhibitors of the binding interaction or of the phosphatase/kinase involved in mediating the interaction.

Immobilized Tyrosine Phosphatase Assay

A phosphorylated peptide mimicking the critical structure of the TCRζ chain was biotinylated and bound to a commercially available microtitre plate pre-coated with streptavidin (Pierce), under mild conditions (e.g. 2.3 μM peptide in TBS containing 0.2% Tween 20 and 1% BSA). A non-phosphorylated analogue was included as a control. The peptide bound to the plate was then treated with a phosphatase under suitable conditions (e.g. 25 mM Tris-HCl pH 7.2, 5 mM EDTA 10 mM β-mercaptoethanol, 50 μg/ml BSA). Alternatively, the peptide was reacted with the phosphatase prior to its binding to the streptavidin-coated plate.

A ZAPSH2 domain was used to detect the phosphorylation status of the peptide on the plate. This SH2 domain was fluorescently labeled with GFP as for the solution phase assay in example 3. The SH2 domain was applied in mild conditions such as PBST/BSA or other suitable buffer. Phosphate dependent binding is determined after washing off excess probe and reading in a suitable instrument. FIG. 7.

Immobilized Src Tyrosine Kinase Assay

Src protein kinase activity can be determined by measuring the transfer of phosphate groups to immobilized substrates, which may be natural binding domains or peptide substrates based on natural binding domains.

Src Kinase Assay with Nickel/NTA Immobilized TCRζ Chain

The TCRζ chain can be expressed and purified with a hexapeptide comprised of histidine residues to facilitate anchoring the protein to a microtitre plate coated with a nickel chelate surface, (Pierce). Immobilization of the domain can be achieved simply by incubating the domain on the plate under suitable conditions (e.g. 50 mM phosphate pH 7, 300 mM NaCl, 5 mM imidazole). Excess protein can be washed off with the binding buffer including 0.2% (v/v) Tween 20. The immobilized substrate can be then reacted with the tyrosine kinase under suitable reaction conditions (e.g. 20 mM Tris-HCl pH 7.2, 1 mM ATP, 10 mM MgCl$_2$, 0.04 mM EDTA, 0.003% (v/v) Brij 35, 0.04 mg/ml BSA, 0.08% (v/v) β-mercaptoethanol). Phosphorylated TCRζ chain can be detected using an SH2 domain fluorescently labeled with GFP as in example 3.

Src Kinase Assay with Biotin/Streptavidin Immobilized TCRζ Chain

Alternatively, the synthetic TCR zeta peptide, peptide 3, was immobilized using a biotin:streptavidin interaction. The peptides were biotinylated under mild conditions using amine or thiol directed chemistry (e.g. 20 mM TES pH 7 for thiol directed labeling, and 200 mM sodium bicarbonate pH 8.3 for amine directed labeling, using 230 μM peptide in the presence of 200 μM label). Biotinylated peptides were bound to a streptavidin-coated plate prior to the kinase reaction, or alternatively, were phosphorylated prior to binding. Phosphorylation of the peptide was achieved using Src kinase under conditions which favor the enzyme activity (e.g. 20 mM Tris-HCl pH 7.2, 1 mM ATP, 10 mM MgCl$_2$, 0.04 mM EDTA, 0.003% (v/v) Brij 35, 0.04 mg/ml BSA, 0.08% (v/v) β-mercaptoethanol Transfer of phosphate groups were detected by use of a GFP labeled SH2 domain as in the previous example. FIG. 8.

I claim:

1. A method for monitoring activity of one or more enzymes comprising the steps of:
   A. mixing:
   (i) one or more tagged binding partner polypeptides;
   (ii) one or more binding partner polypeptides that bind to said one or more tagged binding partner polypeptides of (i); and
   (iii) one or more enzymes that add or remove a moiety to or from said one or more binding partner polypeptides or one or more tagged binding partner polypeptides;
   wherein said one or more binding partner polypeptides are immobilized on a solid support; and
   wherein said one or more tagged binding partner polypeptides or said one or more binding partner polypeptides comprise one or more sites for the addition or removal of said moiety, wherein addition or removal of said moiety promotes binding of said one or more binding partner polypeptides with the corresponding one or more tagged binding partner polypeptides; under conditions which promote binding of said one or more binding partner polypeptides with said one or more tagged binding partners; and
   B. detecting binding of said one or more tagged binding partner polypeptides of (i) to said one or more binding partner polypeptides of (ii), wherein the step of detecting binding comprises adding one or more detector molecules comprising a first region that associates with a tag of said one or more tagged binding partner polypeptides and a second region comprising one or more reporter molecules, wherein detection of binding as a result of said mixing is indicative of enzyme activity.

2. The method of claim 1 wherein both said one or more tagged binding partner polypeptides and said one or more binding partner polypeptides comprise one or more sites for the addition or removal of a moiety.

3. The method of claim 1 wherein said one or more tagged binding partner polypeptides are tagged with one or more fluorescent molecules.

4. The method of claim 3 wherein said detecting comprises monitoring the rate of diffusion of said fluorescent molecule.

5. The method of claim 1 wherein said one or more detector molecules comprise a said first region selected from the group consisting of a coiled-coil, an antigen, an epitope, an antibody, a single chain antibody, an oligonucleotide, avidin and its analogues and derivatives, and streptavidin, its analogs and derivatives; and wherein said one or more detector molecules comprise a said second region selected from the group consisting of an enzyme, a radioisotope, a radionuclide, a fluorochrome, and a fluorescent protein.

6. The method of claim 1 wherein one or more detector molecules are pre-bound to the one or more tagged binding partner polypeptides.

7. The method of claim 1 wherein the tag on said one or more tagged binding partner polypeptides comprises one or more radioactive molecules.

8. The method of claim 7 wherein said detecting comprises monitoring the presence or absence of radioactivity.

9. The method of claim 1 wherein said one or more binding partner polypeptides of step (ii) are tagged.

10. The method of claim 9 wherein the tag on said one or more binding partner polypeptides of step (ii) and said one or more tagged binding partner polypeptides comprises one or more fluorescent molecules.

11. The method of claim 10 wherein said detecting comprises monitoring the presence or absence of fluorescent resonance energy transfer (FRET).

12. The method of claim 1 wherein said one or more sites comprise a sequence which directs modification by an enzyme selected from the group consisting of a kinase, a phosphatase, a UDP-N-acetylglucosamine-dolichyl-phosphate-N-acetylglucosamine phosphotransferase, an O-GlcNAc transferase, a glycylpeptide-N-tetradecanoyl transferase, a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase, and an NAD:Arginine ADP ribosyltransferase.

13. The method of claim 1 wherein said site promotes addition of a chemical moiety selected from the group consisting of a phosphate moiety ($PO_4$), a ubiquitin moiety, a glycosyl moiety, an ADP-ribosyl moiety, a fatty acid moiety, and a sentrin moiety.

14. The method of claim 1 wherein said site promotes removal of a chemical moiety selected from the group consisting of a phosphate moiety ($PO_4$), a ubiquitin moiety, a glycosyl moiety, an ADP-ribosyl moiety, a fatty acid moiety, and a sentrin moiety.

15. The method of claim 1 wherein said tag on said one or more tagged binding partner polypeptides is selected from the group consisting of a coiled-coil, an antigen, an epitope, an antibody, a single chain antibody, a nucleic acid binding domain, a radioactive amino acid, a fluorescent molecule, a reporter enzyme, and biotin.

16. The method of claim 1 wherein said site is recombinant.

17. The method of claim 1 wherein said site is naturally occurring.

18. A method of screening for a candidate modulator of enzymatic activity comprising:
  A. mixing:
    (i) one or more tagged binding partner polypeptides comprising a tag;
    (ii) one or more binding partner polypeptides that bind to said one or more tagged binding partner polypeptides of (i); and
    (iii) one or more enzymes that adds or removes a moiety to or from said binding partner polypeptide or said one or more tagged binding partner polypeptides;
    wherein said one or more binding partner polypeptides are immobilized on a solid support; and
    wherein said one or more tagged binding partner polypeptides or said one or more binding partner polypeptides comprise one or more sites for the addition or removal of said moiety, wherein addition or removal of said moiety promotes binding of said one or more binding partner polypeptides with the corresponding one or more tagged binding partner polypeptides; under conditions which promote binding of said one or more binding partner polypeptides and said one or more tagged binding partner polypeptides; and
  B. detecting binding of said one or more binding partner polypeptides to said one or more tagged binding partner polypeptides in both the presence and absence of a candidate modulator of enzymatic activity, wherein the step of detecting binding comprises adding one or more detector molecules comprising a first region that associates with said tag of said one or more tagged binding partner polypeptides and a second region comprising one or more reporter molecules, wherein detection of an amount of binding in the presence of the candidate modulator that is lesser or greater as compared to the amount of binding in the absence of the candidate modulator indicates modulation of enzymatic activity by said candidate modulator.

* * * * *

SEQUENCE LISTING

```
<160> NUMBER OF SEQ ID NOS: 57

<210> SEQ ID NO 1
<211> LENGTH: 17
<212> TYPE: PRT
<213> ORGANISM: Unknown
<220> FEATURE:
<223> OTHER INFORMATION: ADP-ribosylation domain
<221> NAME/KEY: DOMAIN
<222> LOCATION: (1)..(17)
<223> OTHER INFORMATION: ADT-ribosylation site
```

-continued

```
<400> SEQUENCE: 1

Met Leu Cys Cys Met Arg Arg Thr Lys Gln Val Glu Lys Asn Asp Asp
1               5                   10                  15

Asp

<210> SEQ ID NO 2
<211> LENGTH: 10
<212> TYPE: PRT
<213> ORGANISM: Unknown
<220> FEATURE:
<223> OTHER INFORMATION: ADP-ribosylation site
<221> NAME/KEY: DOMAIN
<222> LOCATION: (1)..(10)
<223> OTHER INFORMATION: ADP-ribosylation site

<400> SEQUENCE: 2

Phe Lys Gln Arg Gln Thr Arg Gln Phe Lys
1               5                   10

<210> SEQ ID NO 3
<211> LENGTH: 30
<212> TYPE: PRT
<213> ORGANISM: Unknown
<220> FEATURE:
<223> OTHER INFORMATION: ubiquitination site
<221> NAME/KEY: DOMAIN
<222> LOCATION: (1)..(30)
<223> OTHER INFORMATION: ubiquitination site

<400> SEQUENCE: 3

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His
            20                  25                  30

<210> SEQ ID NO 4
<211> LENGTH: 21
<212> TYPE: PRT
<213> ORGANISM: Unknown
<220> FEATURE:
<223> OTHER INFORMATION: ubiquitination site
<221> NAME/KEY: DOMAIN
<222> LOCATION: (1)..(21)
<223> OTHER INFORMATION: ubiquitination site

<400> SEQUENCE: 4

His Gly Ser Gly Ala Trp Leu Leu Pro Val Ser Leu Val Lys Arg Lys
1               5                   10                  15

Thr Thr Leu Ala Pro
            20

<210> SEQ ID NO 5
<211> LENGTH: 10
<212> TYPE: PRT
<213> ORGANISM: Unknown
<220> FEATURE:
<223> OTHER INFORMATION: O-GlcNAc site
<221> NAME/KEY: DOMAIN
<222> LOCATION: (1)..(10)
<223> OTHER INFORMATION: O-GlcNAc site

<400> SEQUENCE: 5

Gly Thr Thr Ser Thr Ile Gln Thr Ala Pro
1               5                   10

<210> SEQ ID NO 6
```

```
<211> LENGTH: 12
<212> TYPE: PRT
<213> ORGANISM: Unknown
<220> FEATURE:
<223> OTHER INFORMATION: O-GlcNAc site
<221> NAME/KEY: DOMAIN
<222> LOCATION: (1)..(12)
<223> OTHER INFORMATION: O-GlcNAc site

<400> SEQUENCE: 6

Ser Ala Val Ser Ser Ala Asp Gly Thr Val Leu Lys
1               5                   10

<210> SEQ ID NO 7
<211> LENGTH: 18
<212> TYPE: PRT
<213> ORGANISM: Unknown
<220> FEATURE:
<223> OTHER INFORMATION: O-GlcNAc site
<221> NAME/KEY: DOMAIN
<222> LOCATION: (1)..(18)
<223> OTHER INFORMATION: O-GlcNAc site

<400> SEQUENCE: 7

Asp Ser Ser Thr Asp Leu Thr Gln Thr Ser Ser Ser Gly Thr Val Thr
1               5                   10                  15

Leu Pro

<210> SEQ ID NO 8
<211> LENGTH: 12
<212> TYPE: PRT
<213> ORGANISM: Unknown
<220> FEATURE:
<223> OTHER INFORMATION: O-GlcNAc site
<221> NAME/KEY: DOMAIN
<222> LOCATION: (1)..(12)
<223> OTHER INFORMATION: O-GlcNAc site

<400> SEQUENCE: 8

Met Ala Gly Gly Pro Ala Asp Thr Ser Asp Pro Leu
1               5                   10

<210> SEQ ID NO 9
<211> LENGTH: 13
<212> TYPE: PRT
<213> ORGANISM: Unknown
<220> FEATURE:
<223> OTHER INFORMATION: O-GlcNAc site
<221> NAME/KEY: DOMAIN
<222> LOCATION: (1)..(13)
<223> OTHER INFORMATION: O-GlcNAc site

<400> SEQUENCE: 9

Ala Gln Thr Ile Thr Ser Glu Thr Pro Ser Ser Thr Thr
1               5                   10

<210> SEQ ID NO 10
<211> LENGTH: 8
<212> TYPE: PRT
<213> ORGANISM: Unknown
<220> FEATURE:
<223> OTHER INFORMATION: Consensus sequence
<221> NAME/KEY: MISC_FEATURE
<222> LOCATION: (1)..(8)
<223> OTHER INFORMATION: Xaa at position 6 may be any amino acid
<221> NAME/KEY: MISC_FEATURE
<222> LOCATION: (1)..(8)
<223> OTHER INFORMATION: Xaa at position 3 may be any amino acid

<400> SEQUENCE: 10
```

```
Arg Arg Xaa Arg Arg Xaa Ser Thr
1               5

<210> SEQ ID NO 11
<211> LENGTH: 5
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(5)
<223> OTHER INFORMATION: Consensus sequence, each Xaa is any amino acid
<221> NAME/KEY: MISC_FEATURE
<222> LOCATION: (1)..(5)
<223> OTHER INFORMATION: X at position 2, 3, and 5 can be any amino acid

<400> SEQUENCE: 11

Lys Xaa Xaa Ser Xaa
1               5

<210> SEQ ID NO 12
<211> LENGTH: 3
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(3)
<223> OTHER INFORMATION: Consensus sequence,  Xaa is any amino acid
<221> NAME/KEY: MISC_FEATURE
<222> LOCATION: (1)..(3)
<223> OTHER INFORMATION: X at position 2 can be any amino acid

<400> SEQUENCE: 12

Arg Xaa Thr
1

<210> SEQ ID NO 13
<211> LENGTH: 5
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(5)
<223> OTHER INFORMATION: Consensus sequence, each Xaa is any amino acid
<221> NAME/KEY: MISC_FEATURE
<222> LOCATION: (1)..(5)
<223> OTHER INFORMATION: X at position 2, 3, and 5 can be any amino acid

<400> SEQUENCE: 13

Arg Xaa Xaa Ser Xaa
1               5

<210> SEQ ID NO 14
<211> LENGTH: 4
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(4)
<223> OTHER INFORMATION: Consensus sequence, each Xaa is any amino acid
<221> NAME/KEY: MISC_FEATURE
<222> LOCATION: (1)..(4)
<223> OTHER INFORMATION: X at position 1 and 4 can be any amino acid

<400> SEQUENCE: 14

Xaa Ser Arg Xaa
1
```

```
<210> SEQ ID NO 15
<211> LENGTH: 8
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(8)
<223> OTHER INFORMATION: Consensus sequence, each Xaa is any amino acid
<221> NAME/KEY: MISC_FEATURE
<222> LOCATION: (1)..(8)
<223> OTHER INFORMATION: X at position 1, 3, 4, 6 and 8 can be any amino
      acid

<400> SEQUENCE: 15

Xaa Arg Xaa Xaa Ser Xaa Arg Xaa
1               5

<210> SEQ ID NO 16
<211> LENGTH: 6
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(6)
<223> OTHER INFORMATION: Consensus sequence, each Xaa is any amino acid
<221> NAME/KEY: MISC_FEATURE
<222> LOCATION: (1)..(6)
<223> OTHER INFORMATION: X at position 1, 3, 4, and 6 can be any amino
      acid

<400> SEQUENCE: 16

Xaa Arg Xaa Xaa Ser Xaa
1               5

<210> SEQ ID NO 17
<211> LENGTH: 6
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(6)
<223> OTHER INFORMATION: Consensus sequence

<400> SEQUENCE: 17

Ser Glu Leu Ser Arg Arg
1               5

<210> SEQ ID NO 18
<211> LENGTH: 6
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(6)
<223> OTHER INFORMATION: Consensus sequence, each Xaa is any amino acid
<221> NAME/KEY: MISC_FEATURE
<222> LOCATION: (1)..(6)
<223> OTHER INFORMATION: X at position 1,3,4, and 6 can be any amino
      acid

<400> SEQUENCE: 18

Xaa Ser Xaa Xaa Ser Xaa
1               5

<210> SEQ ID NO 19
<211> LENGTH: 5
```

```
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(5)
<223> OTHER INFORMATION: Consensus sequence, each Xaa is any amino acid
<221> NAME/KEY: MISC_FEATURE
<222> LOCATION: (1)..(5)
<223> OTHER INFORMATION: X at position 1, 3, and 5 can be any amino acid

<400> SEQUENCE: 19

Xaa Ser Xaa Glu Xaa
1               5

<210> SEQ ID NO 20
<211> LENGTH: 7
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(7)
<223> OTHER INFORMATION: Consensus sequence,  each Xaa is any amino acid
<221> NAME/KEY: MISC_FEATURE
<222> LOCATION: (1)..(7)
<223> OTHER INFORMATION: X at poaiation a, 3, 4, 5, and 7 can be any
      amino acid

<400> SEQUENCE: 20

Xaa Ser Xaa Xaa Xaa Ser Xaa
1               5

<210> SEQ ID NO 21
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence

<400> SEQUENCE: 21

Gly Ser Ser Lys Ser Lys Pro Lys Asp
1               5

<210> SEQ ID NO 22
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence

<400> SEQUENCE: 22

Gly Cys Ile Lys Ser Lys Arg Lys Asp
1               5

<210> SEQ ID NO 23
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence
```

```
<400> SEQUENCE: 23

Gly Cys Ile Lys Ser Lys Glu Asp Lys
1               5

<210> SEQ ID NO 24
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence

<400> SEQUENCE: 24

Gly Cys Val Gln Cys Lys Asp Lys Glu
1               5

<210> SEQ ID NO 25
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence

<400> SEQUENCE: 25

Gly Cys Thr Leu Ser Ala Glu Asp Lys
1               5

<210> SEQ ID NO 26
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence

<400> SEQUENCE: 26

Gly Cys Ile Lys Ser Lys Arg Lys Asp
1               5

<210> SEQ ID NO 27
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence

<400> SEQUENCE: 27

Gly Cys Val Gln Cys Lys Asp Lys Glu
1               5

<210> SEQ ID NO 28
<211> LENGTH: 9
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(9)
<223> OTHER INFORMATION: Consensus sequence
```

<400> SEQUENCE: 28

Gly Cys Thr Leu Ser Ala Glu Asp Lys
1               5

<210> SEQ ID NO 29
<211> LENGTH: 4
<212> TYPE: PRT
<213> ORGANISM: Unknown
<220> FEATURE:
<223> OTHER INFORMATION: Consensus sequence
<221> NAME/KEY: DOMAIN
<222> LOCATION: (1)..(4)
<223> OTHER INFORMATION: Consensus sequence, Xaa is any amino acid
<221> NAME/KEY: MISC_FEATURE
<222> LOCATION: (1)..(4)
<223> OTHER INFORMATION: X at position 2 can be any amino acid

<400> SEQUENCE: 29

Asn Xaa Ser Thr
1

<210> SEQ ID NO 30
<211> LENGTH: 4
<212> TYPE: PRT
<213> ORGANISM: Unknown
<220> FEATURE:
<223> OTHER INFORMATION: C-terminal sequence
<221> NAME/KEY: SITE
<222> LOCATION: (1)..(4)
<223> OTHER INFORMATION: C-terminal sequence

<400> SEQUENCE: 30

His Ser Thr Val
1

<210> SEQ ID NO 31
<211> LENGTH: 92
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(92)
<223> OTHER INFORMATION: Synthetic primer

<400> SEQUENCE: 31 gggggagct ctgggaggcg gaggtggagg gctgatgcgc cagctgcagg atgaagttga      60
agaactggaa caggaaaact ggcatctgca ga                                  92

<210> SEQ ID NO 32
<211> LENGTH: 96
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(96)
<223> OTHER INFORMATION: Synthetic primer

<400> SEQUENCE: 32
cccccctcga gttattaaac ttcggcttcc aggcactgaa cttcacgcag cagacgggca    60
acttcgttct gcagatgcca gttttcctgt tccagt                             96

<210> SEQ ID NO 33
<211> LENGTH: 37
<212> TYPE: PRT

```
<213> ORGANISM: Unknown
<220> FEATURE:
<223> OTHER INFORMATION: Coiled-coil sequence
<221> NAME/KEY: DOMAIN
<222> LOCATION: (1)..(37)
<223> OTHER INFORMATION: Coiled coil sequence

<400> SEQUENCE: 33

Leu Met Arg Gln Leu Gln Asp Glu Val Glu Glu Leu Glu Gln Glu Asn
1               5                   10                  15

Trp His Leu Gln Asn Glu Val Ala Arg Leu Leu Arg Glu Val Gln Cys
            20                  25                  30

Leu Glu Ala Glu Val
        35

<210> SEQ ID NO 34
<211> LENGTH: 37
<212> TYPE: PRT
<213> ORGANISM: Unknown
<220> FEATURE:
<223> OTHER INFORMATION: Coiled coil sequence
<221> NAME/KEY: DOMAIN
<222> LOCATION: (1)..(37)
<223> OTHER INFORMATION: Coiled coil sequence

<400> SEQUENCE: 34

Arg Met Arg Gln Leu Glu Asp Arg Val Glu Glu Leu Arg Glu Gln Asn
1               5                   10                  15

Trp His Leu Ala Asn Gln Val Ala Arg Leu Arg Gln Arg Val Cys Glu
            20                  25                  30

Leu Lys Ala Arg Val
        35

<210> SEQ ID NO 35
<211> LENGTH: 80
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(80)
<223> OTHER INFORMATION: Synthetic primer

<400> SEQUENCE: 35
gtaccgctag ctcttacaag ggtattgctc agttggagca ggaaatcgcc caattagaac      60
aagaaaatgc acaacttgaa                                                  80

<210> SEQ ID NO 36
<211> LENGTH: 73
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(61)
<223> OTHER INFORMATION: Synthetic primer

<400> SEQUENCE: 36
gggcatcgat ttcctgctca agctgagcga tctcttgttc aagttgtgca ttttcttgtt      60
ctaattgggc gat                                                         73

<210> SEQ ID NO 37
<211> LENGTH: 31
<212> TYPE: PRT
<213> ORGANISM: Unknown
```

-continued

```
<220> FEATURE:
<223> OTHER INFORMATION: Sequence for cloning
<221> NAME/KEY: DOMAIN
<222> LOCATION: (1)..(31)
<223> OTHER INFORMATION: Sequence for cloning

<400> SEQUENCE: 37

Tyr Lys Gly Ile Ala Gln Leu Glu Gln Glu Ile Ala Gln Leu Glu Gln
1               5                   10                  15

Glu Asn Ala Gln Leu Glu Gln Glu Ile Ala Gln Leu Glu Gln Glu
            20                  25                  30

<210> SEQ ID NO 38
<211> LENGTH: 38
<212> TYPE: PRT
<213> ORGANISM: Unknown
<220> FEATURE:
<223> OTHER INFORMATION: Coiled coil sequence
<221> NAME/KEY: DOMAIN
<222> LOCATION: (1)..(38)
<223> OTHER INFORMATION: Coiled coil sequence

<400> SEQUENCE: 38

Tyr Lys Gly Ile Cys Gln Leu Arg Gln Arg Ile Ala Gln Leu Arg Gln
1               5                   10                  15

Arg Asn Ala Gln Leu Arg Gln Arg Ile Ala Gln Leu Arg Gln Arg Ile
            20                  25                  30

Ala Gln Leu Arg Gln Arg
        35

<210> SEQ ID NO 39
<211> LENGTH: 36
<212> TYPE: PRT
<213> ORGANISM: Artificial Sequence
<220> FEATURE:
<223> OTHER INFORMATION: Synthetic peptide
<221> NAME/KEY: PEPTIDE
<222> LOCATION: (1)..(36)
<223> OTHER INFORMATION: Synthetic peptide

<400> SEQUENCE: 39

Arg Cys Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp
        35

<210> SEQ ID NO 40
<211> LENGTH: 36
<212> TYPE: PRT
<213> ORGANISM: Artificial Sequence
<220> FEATURE:
<223> OTHER INFORMATION: Synthetic peptide
<221> NAME/KEY: PEPTIDE
<222> LOCATION: (1)..(36)
<223> OTHER INFORMATION: Synthetic peptide

<400> SEQUENCE: 40

Arg Cys Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp
        35
```

```
<210> SEQ ID NO 41
<211> LENGTH: 33
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(33)
<223> OTHER INFORMATION: Synthetic primer

<400> SEQUENCE: 41
gggatccata tgccagaccc cgcggcgcac ctg                              33

<210> SEQ ID NO 42
<211> LENGTH: 33
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(33)
<223> OTHER INFORMATION: Synthetic primer

<400> SEQUENCE: 42
ggaattcggg cactgctgtt ggggcaggcc tcc                              33

<210> SEQ ID NO 43
<211> LENGTH: 23
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(23)
<223> OTHER INFORMATION: Synthetic primer

<400> SEQUENCE: 43
gggggcccag agtgaagttc agc                                         23

<210> SEQ ID NO 44
<211> LENGTH: 23
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(23)
<223> OTHER INFORMATION: Synthetic primer

<400> SEQUENCE: 44
gggggcccga gcccccgcg tac                                          23

<210> SEQ ID NO 45
<211> LENGTH: 23
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(23)
<223> OTHER INFORMATION: Synthetic primer

<400> SEQUENCE: 45
gggggcccaa ccagctctat aac                                         23

<210> SEQ ID NO 46
<211> LENGTH: 23
```

```
<212> TYPE: DNA
<213> ORGANISM: Artificial Sequence
<220> FEATURE:
<223> OTHER INFORMATION: Synthetic primer
<221> NAME/KEY: misc_feature
<222> LOCATION: (1)..(23)
<223> OTHER INFORMATION: Synthetic primer

<400> SEQUENCE: 46 gggatccgc gagggggcag ggc                                      23

<210> SEQ ID NO 47
<211> LENGTH: 36
<212> TYPE: PRT
<213> ORGANISM: Artificial Sequence
<220> FEATURE:
<223> OTHER INFORMATION: Synthetic peptide
<221> NAME/KEY: PEPTIDE
<222> LOCATION: (1)..(36)
<223> OTHER INFORMATION: Synthetic peptide

<400> SEQUENCE: 47

Arg Cys Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp
        35

<210> SEQ ID NO 48
<211> LENGTH: 6
<212> TYPE: PRT
<213> ORGANISM: Unknown
<220> FEATURE:
<223> OTHER INFORMATION: Cleavage site
<221> NAME/KEY: MISC_FEATURE
<222> LOCATION: (1)..(6)
<223> OTHER INFORMATION: X at position 6 can be any amino acid
<221> NAME/KEY: SITE
<222> LOCATION: (1)..(6)
<223> OTHER INFORMATION: Clavage site, X can be any mino acid

<400> SEQUENCE: 48

Trp Leu Glu His Asp Xaa
1               5

<210> SEQ ID NO 49
<211> LENGTH: 5
<212> TYPE: PRT
<213> ORGANISM: Unknown
<220> FEATURE:
<223> OTHER INFORMATION: Cleavage site
<221> NAME/KEY: SITE
<222> LOCATION: (1)..(5)
<223> OTHER INFORMATION: Cleavage site, each Xaa is any amino acid
<221> NAME/KEY: MISC_FEATURE
<222> LOCATION: (1)..(5)
<223> OTHER INFORMATION: X at position 3 and 5 can be any amino acid

<400> SEQUENCE: 49

Asp Glu Xaa Asp Xaa
1               5

<210> SEQ ID NO 50
<211> LENGTH: 6
<212> TYPE: PRT
<213> ORGANISM: Unknown
<220> FEATURE:
<223> OTHER INFORMATION: Cleavage site
```

```
<221> NAME/KEY: SITE
<222> LOCATION: (1)..(6)
<223> OTHER INFORMATION: Cleavage site, Xaa is any amino acid
<221> NAME/KEY: MISC_FEATURE
<222> LOCATION: (1)..(6)
<223> OTHER INFORMATION: X at position 4 and 6 can be any amino acid

<400> SEQUENCE: 50

Leu Val Glu Xaa Asp Xaa
1               5

<210> SEQ ID NO 51
<211> LENGTH: 5
<212> TYPE: PRT
<213> ORGANISM: Unknown
<220> FEATURE:
<223> OTHER INFORMATION: Cleavage site
<221> NAME/KEY: SITE
<222> LOCATION: (1)..(5)
<223> OTHER INFORMATION: Cleavage site, Xaa is any amino acid
<221> NAME/KEY: MISC_FEATURE
<222> LOCATION: (1)..(5)
<223> OTHER INFORMATION: X at position 5 can be any amino acid

<400> SEQUENCE: 51

Ile Glu Gly Arg Xaa
1               5

<210> SEQ ID NO 52
<211> LENGTH: 8
<212> TYPE: PRT
<213> ORGANISM: Unknown
<220> FEATURE:
<223> OTHER INFORMATION: Cleavage site
<221> NAME/KEY: SITE
<222> LOCATION: (1)..(8)
<223> OTHER INFORMATION: Cleavage site,  each Xaa is any amino acid
<221> NAME/KEY: MISC_FEATURE
<222> LOCATION: (1)..(8)
<223> OTHER INFORMATION: X at position 3 and 5 can be any amino acid

<400> SEQUENCE: 52

Glu Asn Xaa Tyr Xaa Gln Ser Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Tag peptide
<221> NAME/KEY: PEPTIDE
<222> LOCATION: (1)..(5)
<223> OTHER INFORMATION: Tag peptide

<400> SEQUENCE: 53

Arg Tyr Ile Arg Ser
1               5

<210> SEQ ID NO 54
<211> LENGTH: 6
<212> TYPE: PRT
<213> ORGANISM: Artificial Sequence
<220> FEATURE:
<223> OTHER INFORMATION: Tag peptide
<221> NAME/KEY: PEPTIDE
<222> LOCATION: (1)..(6)
<223> OTHER INFORMATION: Tag peptide

<400> SEQUENCE: 54
```

-continued

```
Asp Thr Tyr Arg Tyr Ile
1               5

<210> SEQ ID NO 55
<211> LENGTH: 6
<212> TYPE: PRT
<213> ORGANISM: Artificial Sequence
<220> FEATURE:
<223> OTHER INFORMATION: Tag peptide
<221> NAME/KEY: PEPTIDE
<222> LOCATION: (1)..(6)
<223> OTHER INFORMATION: Tag peptide

<400> SEQUENCE: 55

Thr Asp Phe Leu Tyr Lys
1               5

<210> SEQ ID NO 56
<211> LENGTH: 9
<212> TYPE: PRT
<213> ORGANISM: Artificial Sequence
<220> FEATURE:
<223> OTHER INFORMATION: Tag peptide
<221> NAME/KEY: PEPTIDE
<222> LOCATION: (1)..(9)
<223> OTHER INFORMATION: Tag sequence

<400> SEQUENCE: 56

Glu Glu Glu Glu Tyr Met Pro Met Glu
1               5

<210> SEQ ID NO 57
<211> LENGTH: 11
<212> TYPE: PRT
<213> ORGANISM: Artificial Sequence
<220> FEATURE:
<223> OTHER INFORMATION: Tag peptide
<221> NAME/KEY: PEPTIDE
<222> LOCATION: (1)..(11)
<223> OTHER INFORMATION: Tag sequence

<400> SEQUENCE: 57

Lys Pro Pro Thr Pro Pro Pro Glu Pro Glu Thr
1               5                   10
```